(12) United States Patent
Yamagata et al.

(10) Patent No.: US 7,541,099 B2
(45) Date of Patent: Jun. 2, 2009

(54) ANTHRACENE DERIVATIVE AND LIGHT EMITTING ELEMENT AND LIGHT EMITTING DEVICE USING THE SAME

(75) Inventors: Sachiko Yamagata, Atsgui (JP); Ryoji Nomura, Yamato (JP); Kumi Kojima, Isehara (JP); Satoshi Seo, Kawasaki (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 589 days.

(21) Appl. No.: 11/118,371

(22) Filed: May 2, 2005

(65) Prior Publication Data

US 2005/0260450 A1    Nov. 24, 2005

(30) Foreign Application Priority Data

May 21, 2004    (JP)    ............................. 2004-152567

(51) Int. Cl.
*H01L 51/50*    (2006.01)
*C09K 11/06*    (2006.01)
*C07C 211/00*    (2006.01)

(52) U.S. Cl. ...................... 428/690; 428/917; 313/504; 313/506; 564/433; 564/434; 585/26

(58) Field of Classification Search ................. 313/504, 313/506; 564/433, 434; 585/26
See application file for complete search history.

(56) References Cited

U.S. PATENT DOCUMENTS

| 5,972,247 | A | 10/1999 | Shi et al. |
| 6,743,948 | B1 | 6/2004 | Hosokawa et al. |
| 6,929,871 | B2 | 8/2005 | Arakane et al. |

(Continued)

FOREIGN PATENT DOCUMENTS

JP    2001-131541    5/2001

OTHER PUBLICATIONS

Danel et al., Chemical Materials, (2002), vol. 14, p. 3860-3865.*

(Continued)

*Primary Examiner*—Dawn Garrett
(74) *Attorney, Agent, or Firm*—Eric J. Robinson; Robinson Intellectual Property Law Office, P.C.

(57) ABSTRACT

It is an object of the present invention to provide a luminescent material that has resistance to repeated oxidation reactions. Further, it is an object of the present invention to provide a light-emitting element that is high in luminous efficiency. Further, it is an object of the present invention to provide a light-emitting element that has a long life. An aspect of the present invention is an anthracene derivative represented by a general formula (1). In the general formula (1), $R^2$ to $R^4$ and $R^7$ to $R^9$ are individually any one of hydrogen, an alkyl group having 1 to 4 carbon atoms, and a group represented by the following structure formula (2), and $R^1$, $R^5$, $R^6$, and $R^{10}$ are individually any one of hydrogen and an alkyl group having 1 to 4 carbon atoms.

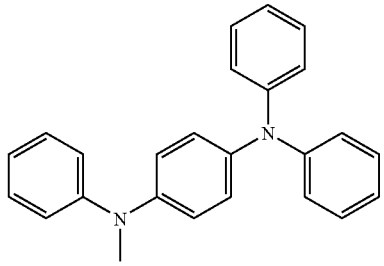

(2)

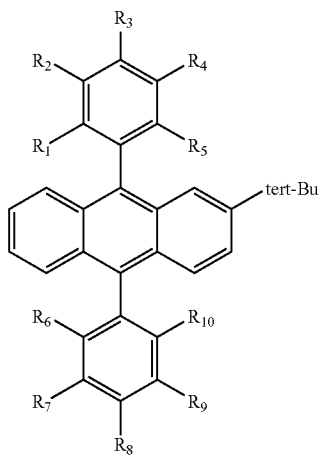

(1)

14 Claims, 15 Drawing Sheets

U.S. PATENT DOCUMENTS

| | | | |
|---|---|---|---|
| 2002/0037429 A1* | 3/2002 | Sato et al. | 428/690 |
| 2003/0072966 A1 | 4/2003 | Hosokawa et al. | |
| 2003/0143430 A1* | 7/2003 | Kawamura et al. | 428/690 |
| 2004/0018380 A1* | 1/2004 | Aziz et al. | 428/690 |
| 2005/0038296 A1 | 2/2005 | Hosokawa et al. | |
| 2006/0043858 A1* | 3/2006 | Ikeda et al. | 313/250 |
| 2007/0152572 A1* | 7/2007 | Kawakami et al. | 313/505 |

OTHER PUBLICATIONS

Office Action (Application No. 200510073741.3) dated Jan. 16, 2009.

Balaganesan.B et al., "Synthesis of t-butylated diphenylanthracene derivatives as blue host materials for OLED applications," Tetrahedron Letters, 2003, vol. 44, pp. 5747-5750.

* cited by examiner

ANTHRACENE DERIVATIVE AND LIGHT EMITTING ELEMENT AND LIGHT EMITTING DEVICE USING THE SAME

BACKGROUND OF THE INVENTION

1. Field of the Invention

The present invention relates to an anthracene derivative, and particular relates to an anthracene derivative that can be used as a material for a light-emitting element.

2. Description of the Related Art

In these years, many of light-emitting elements that are used in displays and the like have a structure in which a layer including a luminescent material is sandwiched between a pair of electrodes. In these light-emitting elements, light is emitted when an exciton formed by recombination of an electron injected from one of the electrodes and a hole injected from the other electrode returns to the ground state.

In the field of light-emitting elements, the structure of a layer including a luminescent material, a novel material for forming a layer including a luminescent material, or the like has been developed in order to obtain a light-emitting element that is superior in luminous efficiency and color purity or is able to prevent quenching or the like.

For example, in Patent Document 1, a material that is high in luminous efficiency, has a long life, and is used for an organic EL element is disclosed.

Now then, in a light-emitting element, current flows between electrodes by transfer of holes or electrons. In this case, a luminescent material or the like that has holes or electrons received, that is, an oxidized or reduced luminescent material or the like, sometimes changes to have different properties without returning to the neutral. Further, when such change in properties of the luminescent material is accumulated, there is a possibility that characteristics of the light-emitting element change.

Therefore, development of a luminescent material that is unlikely to change in properties by oxidation or reduction has been required.

(Patent Document 1) Japanese Patent Application Laid-Open No. 2001-131541

SUMMARY OF THE INVENTION

It is an object of the present invention to provide a luminescent material that has resistance to repeated oxidation reactions. Further, it is an object of the present invention to provide a light-emitting element that is high in luminous efficiency. Further, it is an object of the present invention to provide a light-emitting element that has a long life.

An aspect of the present invention is an anthracene derivative represented by a general formula (1).

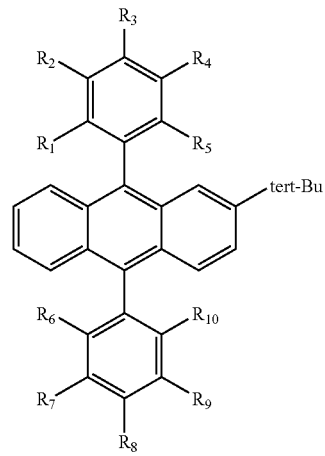

(1)

In the general formula (1), $R^2$ to $R^4$ and $R^7$ to $R^9$ are individually any one of hydrogen, an alkyl group having 1 to 4 carbon atoms, and a group represented by the following structure formula (2), and $R^1$, $R^5$, $R^6$, and $R^{10}$ are individually any one of hydrogen and an alkyl group having 1 to 4 carbon atoms.

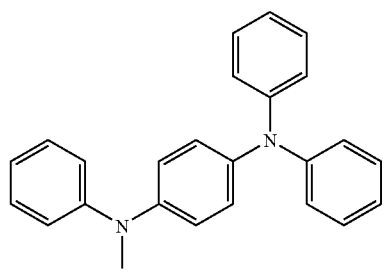

(2)

Another aspect of the present invention is an anthracene derivative represented by a general formula (3).

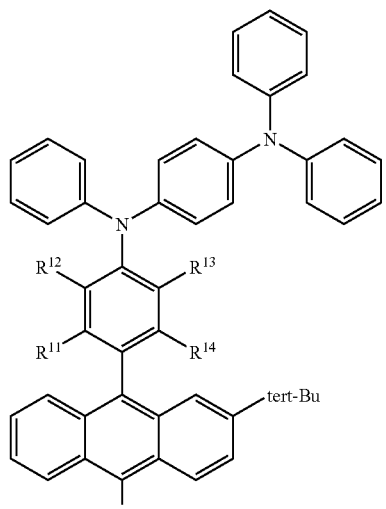

(3)

-continued

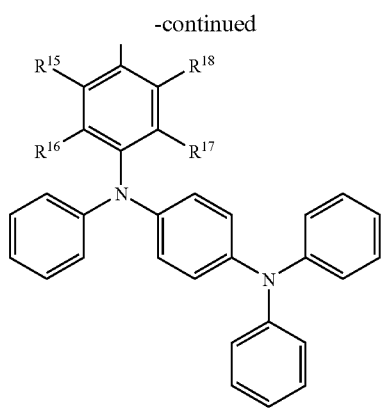

In the general formula (3), $R^{11}$ to $R^{18}$ are individually any one of hydrogen and an alkyl group having 1 to 4 carbon atoms, or $R^{11}$ and $R^{12}$, $R^{13}$ and $R^{14}$, $R^{15}$ and $R^{16}$, and $R^{17}$ and $R^{18}$ are individually bonded to form an aromatic ring. It is to be noted that the bond of $R^{11}$ and $R^{12}$, the bond of $R^{13}$ and $R^{14}$, the bond of $R^{15}$ and $R^{16}$, and the bond of $R^{17}$ and $R^{18}$ are independent of one another.

Another aspect of the present invention is an anthracene derivative represented by a general formula (4).

(4)

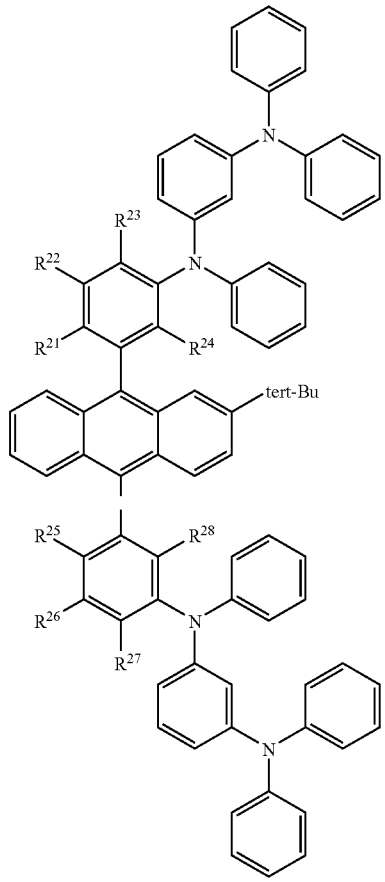

In the general formula (4), $R^{21}$ to $R^{28}$ are individually any one of hydrogen and an alkyl group having 1 to 4 carbon atoms, or $R^{21}$ and $R^{22}$, $R^{22}$ and $R^{23}$, $R^{25}$ and $R^{26}$, and $R^{26}$ and $R^{27}$ are individually bonded to form an aromatic ring. It is to be noted that the bond of $R^{21}$ and $R^{22}$, the bond of $R^{22}$ and $R^{23}$, the bond of $R^{25}$ and $R^{26}$, and the bond of $R^{26}$ and $R^{27}$ are independent of one another.

Another aspect of the present invention is an anthracene derivative represented by a general formula (5).

(5)

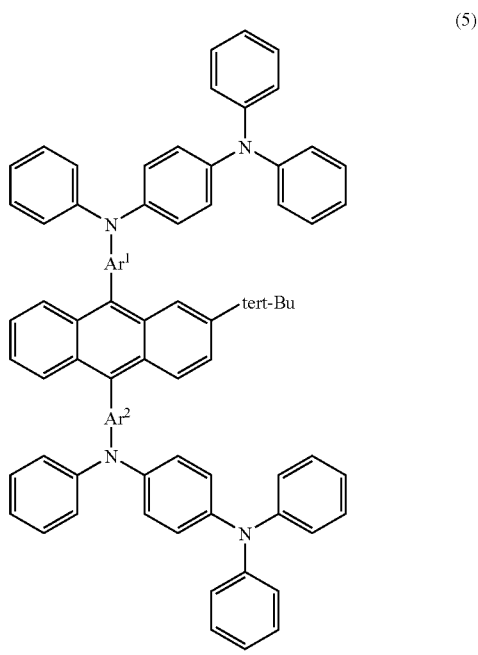

In the general formula (5), $Ar^1$ and $Ar^2$ are individually an aryl group having 6 to 14 carbon atoms. It is to be noted that the aryl group may have a substituent, for example, a substituent having 1 to 4 carbon atoms.

Another aspect of the present invention is a light-emitting element including the anthracene derivative represented by any one of the general formulas (1), (3), (4), and (5).

Another aspect of the present invention is a light-emitting device using a light-emitting element including the anthracene derivative represented by any one of the general formulas (1), (3), (4), and (5).

Another aspect of the present invention is a light-emitting device that has, in a pixel portion, a light-emitting element including the anthracene derivative represented by any one of the general formulas (1), (3), (4), and (5).

Another aspect of the present invention is an electronic device in which a light-emitting device using a light-emitting element including the anthracene derivative represented by any one of the general formulas (1), (3), (4), and (5) is mounted.

According to the present invention, a light-emitting element that has great resistance to repeated oxidation reactions can be obtained. In addition, a light-emitting element that has little change in characteristics associated with change in properties of a luminescent material due to repeated oxidation reactions and shows stable light emission for a long periodcan be obtained. In addition, a light-emitting element that emits light efficiently can be obtained by using an anthracene derivative according to the present invention.

DETAILED DESCRIPTION OF THE INVENTION

EMBODIMENT 1

Examples of anthracene derivatives according to the present invention will be described.

Anthracene derivatives according to the present invention include anthracene derivatives represented by structure formulas (6) to (9).

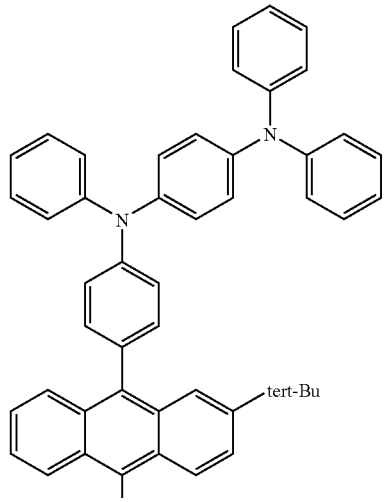

(6)

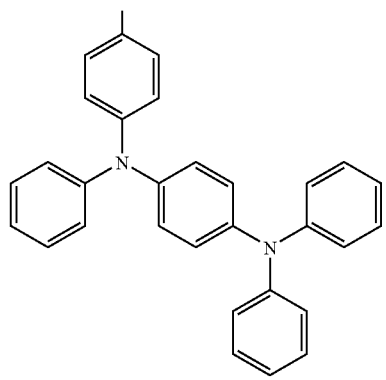

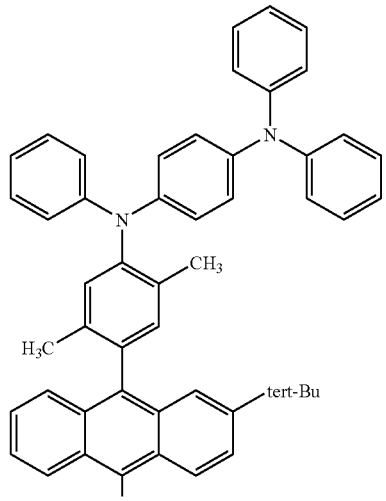

(7)

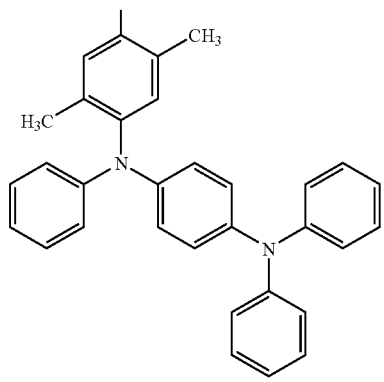
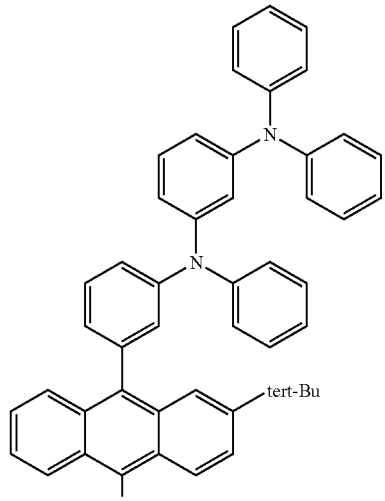
(8)
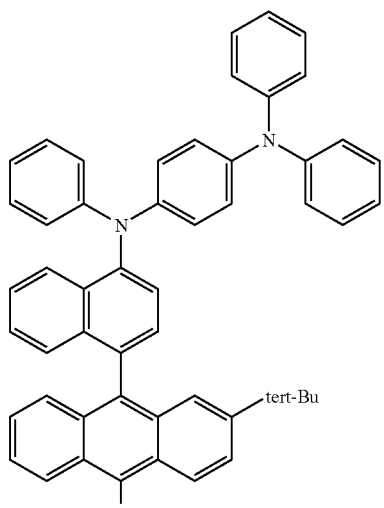
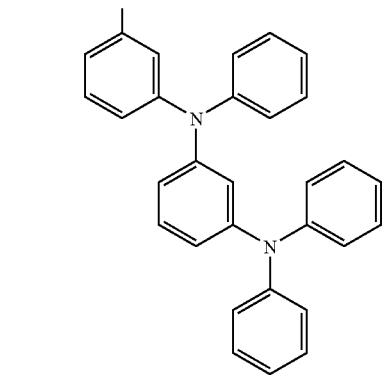
These anthracene derivatives are synthesized in accordance with the following synthesis scheme (a-1) or (a-2).
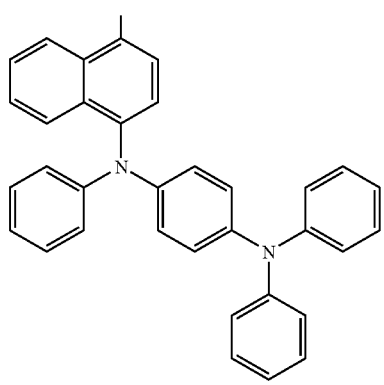
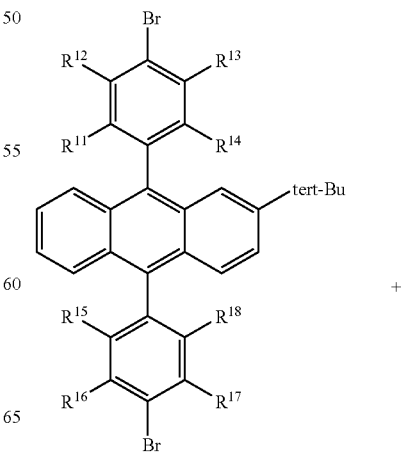

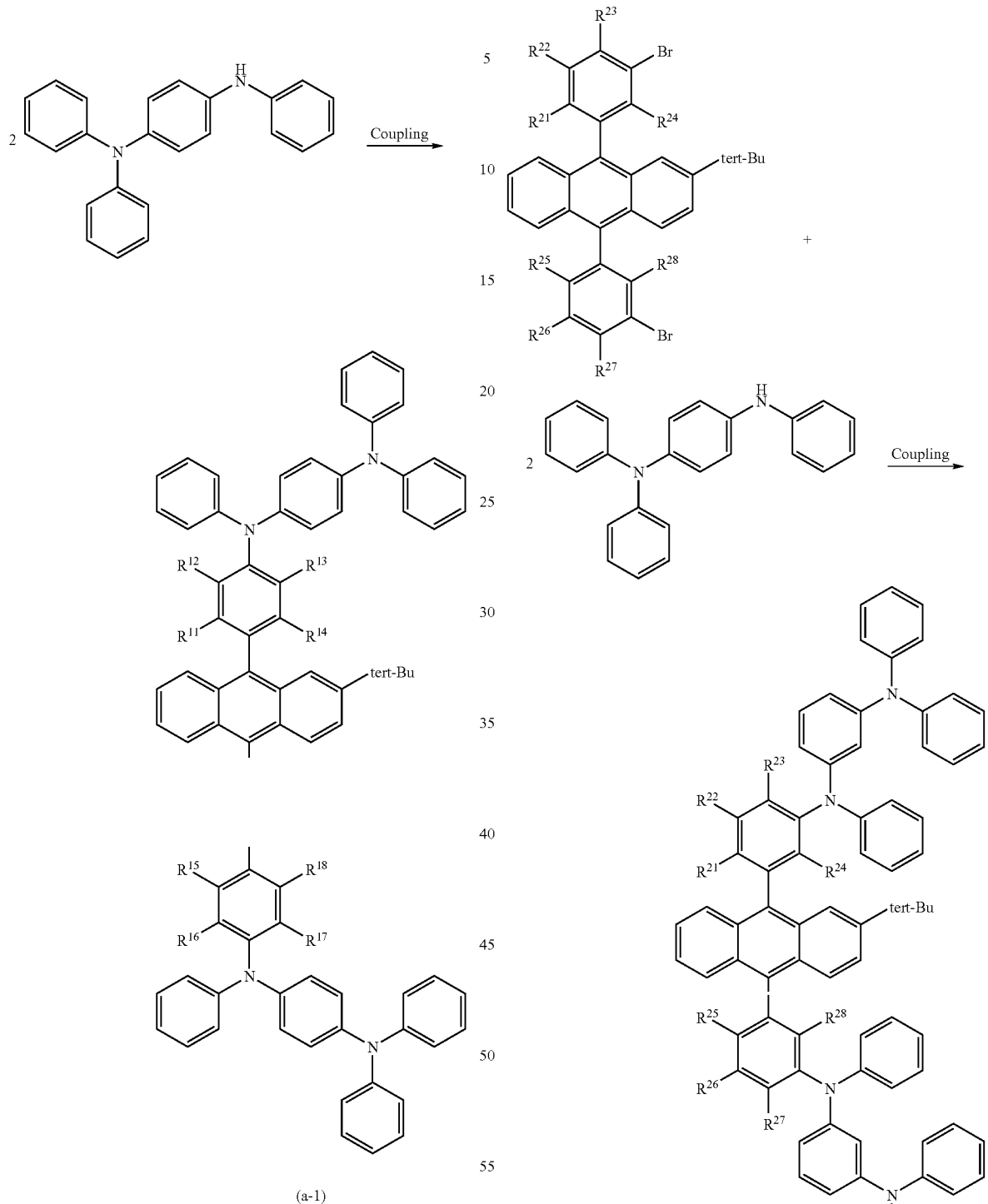

In the synthesis scheme (a-1), $R^{11}$ to $R^{18}$ are individually any one of hydrogen and an alkyl group having 1 to 4 carbon atoms, or $R^{11}$ and $R^{12}$, $R^{13}$ and $R^{14}$, $R^{15}$ and $R^{16}$, and $R^{17}$ and $R^{18}$ are individually bonded to form an aromatic ring. It is to be noted that the bond of $R^{11}$ and $R^{12}$, the bond of $R^{13}$ and $R^{14}$, the bond of $R^{15}$ and $R^{16}$, and the bond of $R^{17}$ and $R^{18}$ are independent of one another.

In the synthesis scheme (a-2), $R^{21}$ to $R^{28}$ are individually any one of hydrogen and an alkyl group having 1 to 4 carbon atoms, or $R^{21}$ and $R^{22}$, $R^{22}$ and $R^{23}$, $R^{25}$ and $R^{26}$, and $R^{26}$ and $R^{27}$ are individually bonded to form an aromatic ring. It is to be noted that the bond of $R^{21}$ and $R^{22}$, the bond of $R^{22}$ and $R^{23}$, the bond of $R^{25}$ and $R^{26}$, and the bond of $R^{26}$ and $R^{27}$ are independent of one another.

The above-described anthracene derivatives according to the present invention have resistance to the repeated oxidation reactions. In addition, the above-described anthracene derivatives according to the present invention are able to show blue or bluish luminescence.

EMBODIMENT 2

The structure of a light-emitting element using an anthracene derivative according to the present invention as a luminescent material will be described with reference to FIG. 1.

Figure 1:
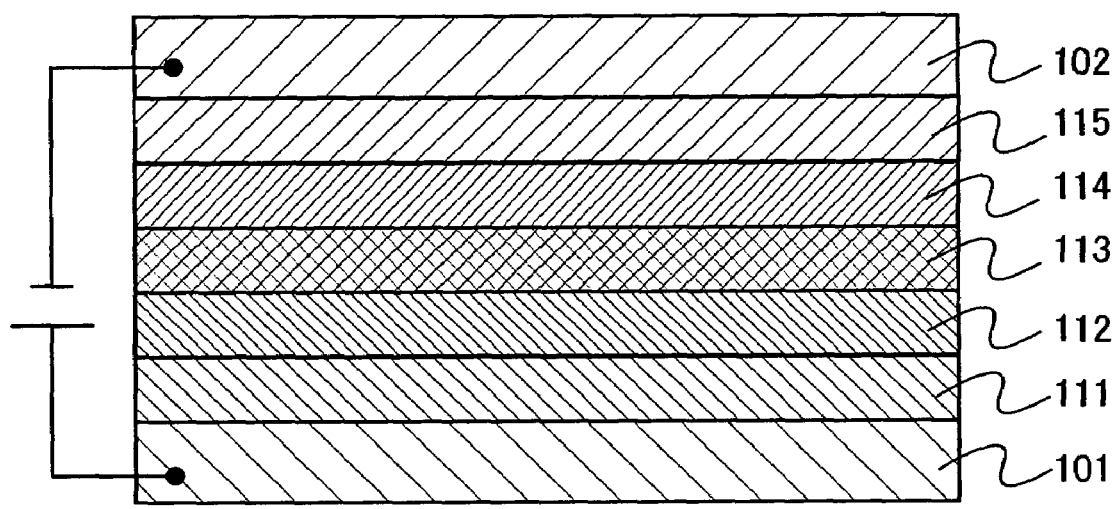
FIG. 1 is a diagram illustrating a light-emitting element according to the present invention.

FIG. 1 shows a light-emitting element that has a light-emitting layer 113 between a first electrode 101 and a second electrode 102. In the light-emitting layer 113, an anthracene derivative represented by any one of the general formulas (1), (3), (4), and (5) and the structure formulas (6) to (9) according to the present invention is included.

In this light-emitting element, a hole emitted from the first electrode 101 and an electron injected from the second electrode 102 are recombined in the light-emitting layer 113 to bring the anthracene derivative according to the present invention to an excited state. Then, light is emitted when the anthracene derivative according to the present invention in the excited state returns to the ground state. As just described, the anthracene derivative according to the present invention serves as a luminescent material. It is to be noted that the first electrode 101 and the second electrode 102 respectively serve as an anode and a cathode in the light-emitting element in the present embodiment.

Here, the light-emitting layer 113 is not particularly limited. However, it is preferable that the light-emitting layer 113 be a layer in which the anthracene derivative according to the present invention is included so as to be dispersed as a guest material in a layer composed of a material that has a larger energy gap than the anthracene derivative. This makes it possible to prevent quenching of luminescence from the anthracene derivative according to the present invention due to a concentration. It is to be noted that an energy gap indicates an energy gap between a LUMO level and a HOMO level.

The material (host material) to be used for dispersing the anthracene derivative according to the present invention is not particularly limited. However, metal complexes such as bis [2-(2-hydroxyphenyl)-pyridinato]zinc (abbreviation: $Znpp_2$) and bis[2-(2-hydroxyphenyl)-benzoxazolato]zinc (abbreviation: ZnBOX) are preferable in addition to an anthracene derivative such as 9,10-di(2-naphthyl)-2-tert-butylanthracene (abbreviation: t-BuDNA) and a carbazole derivative such as 4,4'-bis(N-carbazolyl)-biphenyl (abbreviation: CBP).

Although the first electrode 101 is not particularly limited, it is preferable that the first electrode 101 is formed by using a material that has a larger work function when the first electrode 101 functions as an anode as in the present embodiment. Specifically, in addition to indium tin oxide (ITO), indium tin oxide including silicon oxide, and indium oxide including zinc oxide at 2 to 20%, gold (Au), platinum (Pt), nickel (Ni),. tungsten (W), chromium (Cr), molybdenum (Mo), iron (Fe), cobalt (Co), copper (Cu), palladium (Pd), and the like can be used. The first electrode 101 can be formed by, for example, sputtering or evaporation.

In addition, although the second electrode 102 is not particularly limited, it is preferable that the second electrode 102 is formed by using a material that has a smaller work function when the second electrode 102 functions as a cathode as in the present embodiment. Specifically, aluminum containing an alkali metal or an alkali-earth metal such as lithium (Li) or magnesium, and the like can be used. The second electrode 102 can be formed by, for example, sputtering or evaporation.

Further, in order to extract emitted light to the outside, it is preferable that any one or both of the first electrode 101 and the second electrode 102 be an electrode composed of a material such as indium tin oxide or an electrode formed to be several to several tens nm in thickness so that visible light can be transmitted.

In addition, a hole transporting layer 112 may be provided between the first electrode 101 and the light-emitting layer 113 as shown in FIG. 1. Here, a hole transporting layer is a layer that has a function of transporting holes injected from the first electrode 101 to the light-emitting layer 113. By providing the hole transporting layer 112 to keep the first electrode 101 away from the light-emitting element 113 in this way, quenching of emission due to a metal can be prevented.

The hole transporting layer 112 is not particularly limited, and it is possible to use a layer formed with the use of, for example, an aromatic amine compound (that is, compound including a bond of a benzene ring-nitrogen) such as 4,4'-bis [N-(1-naphthyl)-N-phenyl-amino]-biphenyl (abbreviation: α-NPD), 4,4'-bis[N-(3-methylphenyl)-N-phenyl-amino]-biphenyl (abbreviation: TPD), 4,4',4"-tris(N,N-diphenyl-amino)-triphenylamine (abbreviation: TDATA), or 4,4',4"-tris[N-(3-methylphenyl)-N-phenyl-amino]-triphenylamine (abbreviation: MTDATA).

In addition, the hole transporting layer 112 may be a layer that has a multilayer structure formed by combining two or more layers each including the material mentioned above.

Further, an electron transporting layer 114 may be provided between the second electrode 102 and the light-emitting layer 113 as shown in FIG. 1. Here, an electron transporting layer is a layer that has a function of transporting electrons injected from the second electrode 102 to the light-emitting layer 113. By providing the electron transporting layer 114 to keep the second electrode 102 away from the light-emitting element 113 in this way, quenching of emission due to a metal can be prevented.

The electron transporting layer 114 is not particularly limited, and it is possible to use a layer formed with the use of, for example, a metal complex including a quinoline skeleton or a benzoquinoline skeleton such as tris (8-quinolinolato) aluminum (abbreviation: $Alq_3$), tris(4-methyl-8-quinolinolato) aluminum (abbreviation: $Almq_3$), bis(10-hydroxybenzo [h]quinolinato) beryllium (abbreviation: $BeBq_2$), or bis(2-methyl-8-quinolinolato)-4-phenylphenolato-aluminum (abbreviation: BAlq). In addition, a layer formed with the use of, for example, a metal complex including a oxazole-based ligand or a thiazole-based ligand such as bis[2-(2-hydroxyphenyl)-benzoxazolato]zinc (abbreviation: $Zn(BOX)_2$) or bis[2-(2-hydroxyphenyl)-benzothiazolato]zinc (abbreviation: $Zn(BTZ)_2$), may be used. Further, a layer formed with the use of 2-(4-biphenylyl)-5-(4-tert-butylphenyl)-1,3,4-oxadiazole (abbreviation: PBD), 1,3-bis[5-(p-tert-butylphenyl)-1,3,4-oxadiazole -2-yl]benzene (abbreviation: to as OXD-7), 3-(4-tert-butylphenyl)-4-phenyl-5-(4-biphenylyl)-1,2,4-triazole (abbreviation: TAZ),3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproin (abbreviation: BCP) or the like may be used.

In addition, the electron transporting layer 114 may be a layer that has a multilayer structure formed by combining two or more layers each including the material mentioned above.

Further, a hole injecting layer may be provided between the first electrode 101 and the hole transporting layer 112 as shown in FIG. 1. Here, a hole injecting layer is a layer that has a function of assisting injection of holes from an electrode to serve as an anode to the hole transporting layer 112. It is to be noted that injection of holes into a light-emitting layer may be assisted by providing a hole injecting layer between an electrode to serve as an anode and the light-emitting layer when no hole transporting layer is particularly provided.

The hole injecting layer 111 is not particularly limited, and it is possible to use a layer formed with the use of, for example, a metal oxide such as molybdenum oxide (MoOx), vanadium oxide (VOx), ruthenium oxide (RuOx), tungsten oxide (WOx), manganese oxide (MnOx). In addition, the hole injecting layer 111 can be formed with the use of a phthalocyanine compound such as phthalocyanine (abbreviation: $H_2Pc$) or copper phthalocyanine (abbreviation: CuPc), a poly(ethylenedioxythiophene)/poly(styrene sulfonate) aqueous solution (PEDOT/PSS), or the like.

Further, an electron injecting layer 115 may be provided between the second electrode 102 and the electron transporting layer 114 as shown in FIG. 1. Here, an electron injecting layer is a layer that has a function of assisting injection of electrons from an electrode to serve as a cathode to the electron transporting layer 114. It is to be noted that injection of electrons into a light-emitting layer may be assisted by providing an electron injecting layer between an electrode to serve as a cathode and the light-emitting layer when no electron transporting layer is particularly provided.

The electron injecting layer 115 is not particularly limited, it is possible to use a layer formed with the use of, for example, a compound of an alkali metal or an alkali-earth metal such as lithium fluoride (LiF), cesium fluoride (CsF), or calcium fluoride ($CaF_2$). In addition, a layer in which a highly electron-transporting material such as $Alq_3$ or 4,4-bis(5-methylbenzoxazol-2-yl) stilbene (abbreviation: BzOs) is mixed with an alkali metal or an alkali-earth metal such as magnesium or lithium can also be used as the electron injecting layer 115.

In the above-described light-emitting element according to the present invention, each of the hole injecting layer 111, the hole transporting layer 112, the light-emitting layer 113, the electron transporting layer 114, and the electron injecting layer 115 may be formed by any one method of evaporation, inkjet, and coating. In addition, the first electrode 101 and the second electrode 102 may be formed by any one method of sputtering and evaporation.

Since the light-emitting element according to the present invention, which has a structure as described above, has the anthracene derivative according to the present invention, the light-emitting element has little change in characteristics associated with change in properties of a luminescent material due to repeated oxidation reactions, and shows stable light emission for a long period. In addition, since the light-emitting element according to the present invention, which has a structure as described above, the anthracene derivative according to the present invention, the light-emitting element is able to emit light efficiently.

EMBODIMENT 3

The light-emitting element according to the present invention, which is described in Embodiment 2, can be applied to a pixel portion of a light-emitting device that has a display function and a lighting portion of a light-emitting device that has a lighting function. Further, since the light-emitting element according to the present invention is capable of emitting light efficiently, a light-emitting device that is lower in power consumption by using the light-emitting element according to the present invention. In addition, since the light-emitting element according to the present invention has a long life, favorable display images or the like can be provided for a long period.

In the present embodiment, a circuit configuration and driving method of a light-emitting device that has a display function will be described with reference to FIGS. 3 to 6.

Figure 3:
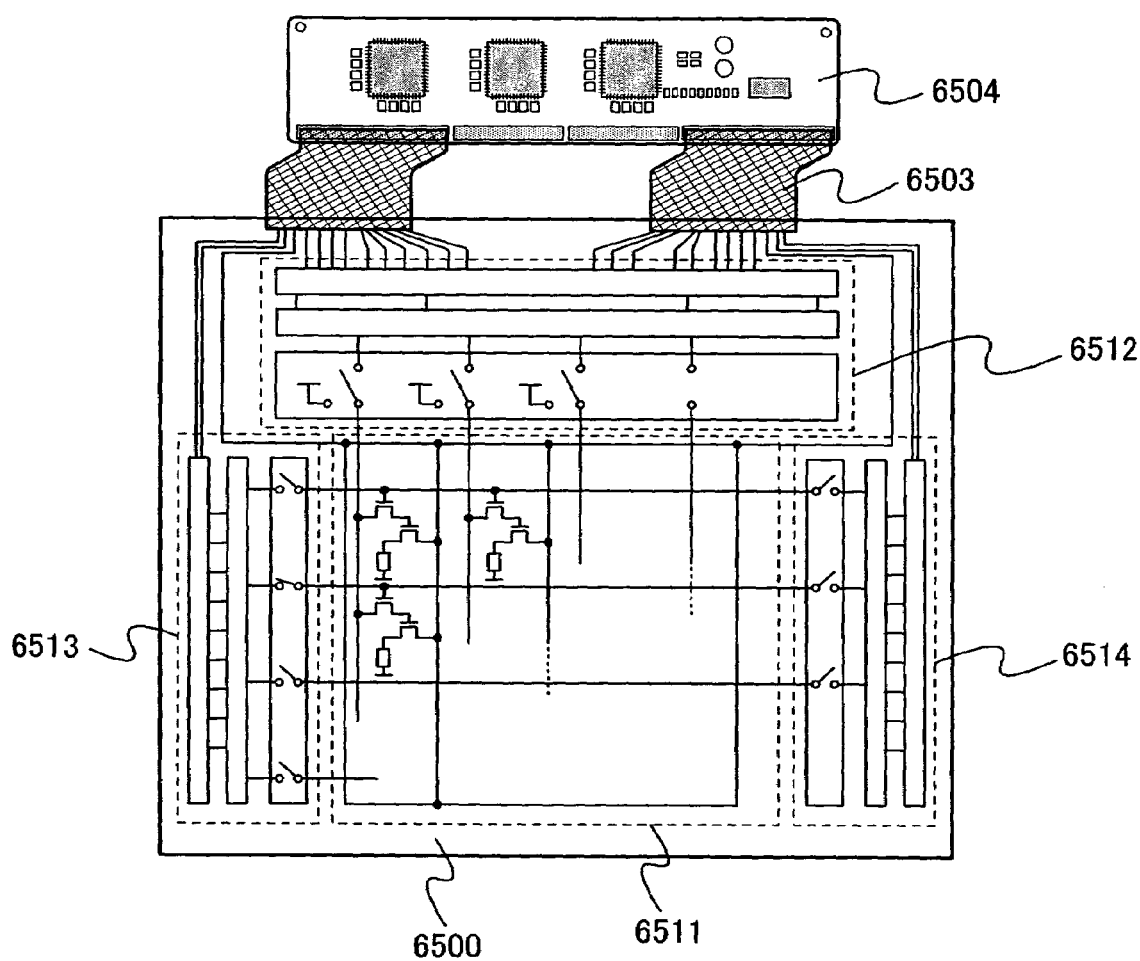
FIG. 3 is a diagram illustrating a light-emitting device according to the present invention.

FIG. 3 is an overhead schematic view of a light-emitting device to which the present invention is applied. In FIG. 3, a pixel portion 6511, a source signal line driver circuit 6512, a gate signal line driver circuit 6513 for writing, and a gate signal line driver circuit 6514 for erasing are provided over a substrate 6500. Each of the source signal line driver circuit 6512, the gate signal line driver circuit 6513 for writing, and the gate signal line driver circuit 6514 for erasing is connected to FPC (Flexible Printed Circuit) 6503 that is an external input terminal through a group of wirings. Further, each of the source signal line driver circuit 6512, the gate signal line driver circuit 6513 for writing, and the gate signal line driver circuit 6514 for erasing receives signals such as a clock signal, a start signal, and a reset signal from the FPC 6503. In addition, a printed wiring board (PWB) 6504 is attached to the FPC 6503. It is to be noted that it is not always necessary to provide the driver circuit portion on the same substrate on which the pixel portion 6511 is provided as described above. For example, the driver circuit portion may be provided outside the substrate by using a TCP that has an IC chip on an FPC on which a wiring pattern is formed.

In the pixel portion 6511, a plurality of source signal lines extending in columns is arranged in rows, current supply lines are arranged in rows, and a plurality of gate signal lines extending in rows is arranged in columns. Further, in the pixel portion 6511, a plurality of circuits each including a light-emitting element is arranged.

Figure 4:
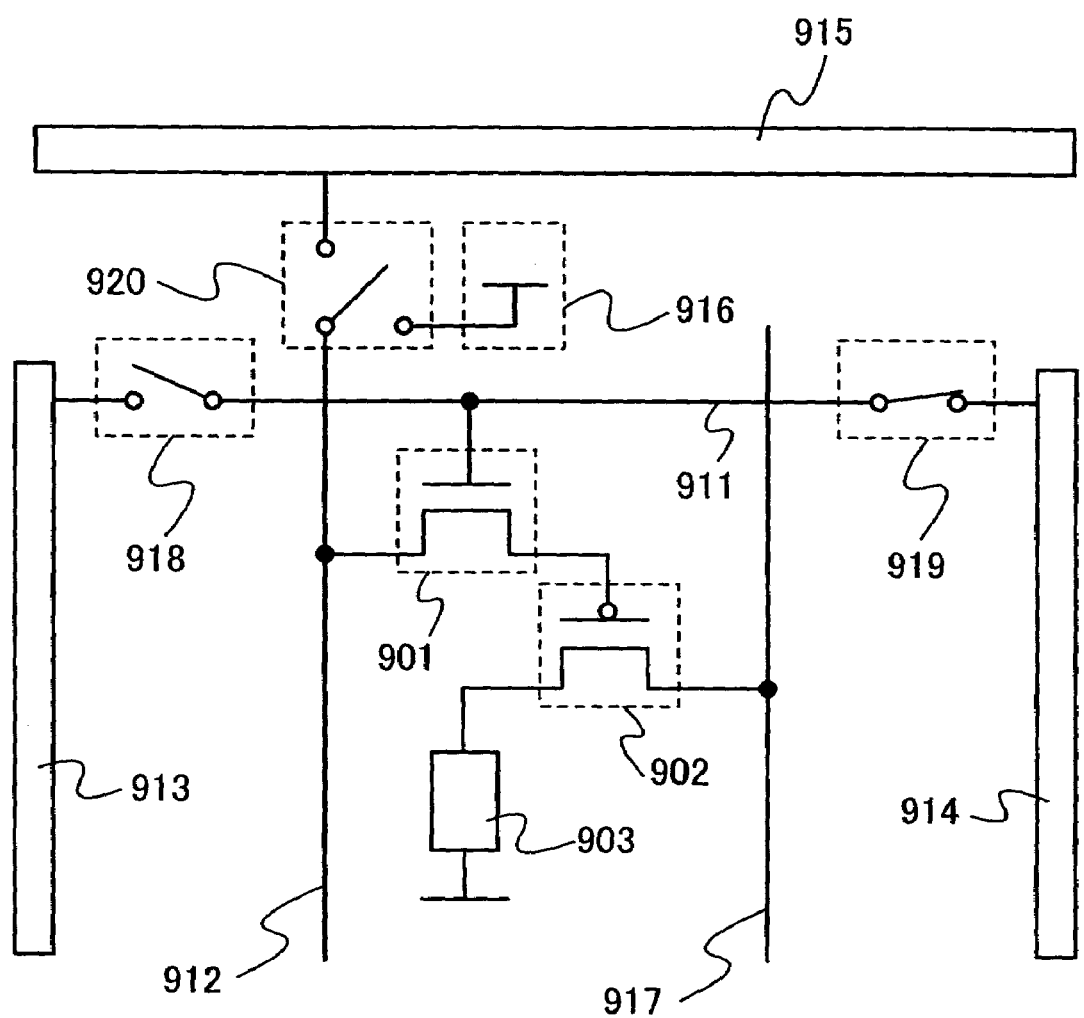
FIG. 4 is a diagram illustrating a circuit included in a light-emitting device according to the present invention.

FIG. 4 is a diagram showing a circuit for operating one pixel. The circuit shown in FIG. 4 includes a first transistor 901, a second transistor 902, and a light-emitting element 903.

Each of the first transistor 901 and the second transistor 902 is a three-terminal element including a gate electrode, a drain region, and a source region, and including a channel region between the drain region and the source region. Here, since a source region and a drain region are switched with each other in accordance with a structure or operating conditions of a transistor, it is difficult to identify which one is the drain region or the source region. Consequently, regions that serve as a source or a drain are referred to as first and second electrodes in the present embodiment.

A gate signal line 911 and a gate signal line driver circuit 913 for writing are provided so as to be electrically connected or unconnected by a switch 918, the gate signal line 911 and a gate signal line driver circuit 914 for erasing are provided so as to be electrically connected or unconnected by a switch 919, and a source signal line 912 is provided so as to be electrically connected to any one of a source signal line driver circuit 915 and a power source 916 by a switch 920. Further, the first transistor 901 has a gate electrically connected to the gate signal line 911, a first electrode electrically connected to the source signal line 912, and a second electrode electrically connected to a gate electrode of the second transistor 902. The second transistor 902 has a first electrode electrically connected to a current supply line 917 and a second electrode electrically connected to one electrode included in the light-emitting element 903. It is to be noted that the switch 918 may be included in the gate signal line driver circuit 913 for writing, the switch 919 may be included in the gate signal line driver circuit 914 for erasing, and the switch 920 may be included in the source signal line driver circuit 915.

Figure 5:
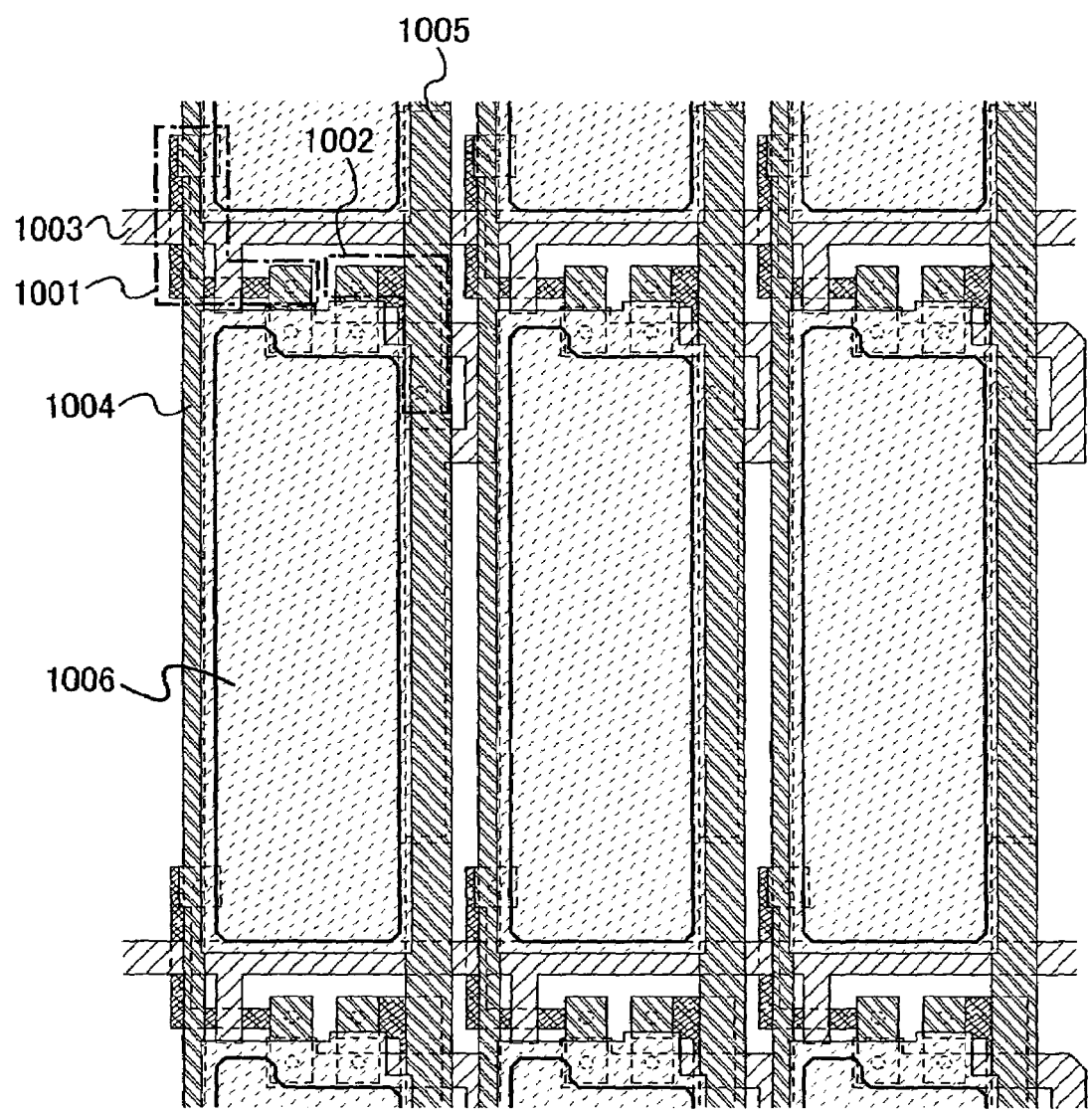
FIG. 5 is a top view of a light-emitting device according to the present invention.

In addition, arrangement of a transistor, a light-emitting element, and the like is not particularly limited. For example, arrangement shown in a top view of FIG. 5 can be employed. In FIG. 5, a first transistor 1001 has a first electrode connected to a source signal line 1004 and a second electrode connected to a gate electrode of a second transistor 1002. Further, the second transistor 1002 has a first electrode connected to a current supply line 1005 and a second electrode connected an electrode 1006 of a light-emitting element. A portion of a gate signal line 1003 serves as a gate electrode of the first transistor 1001.

Figure 6:
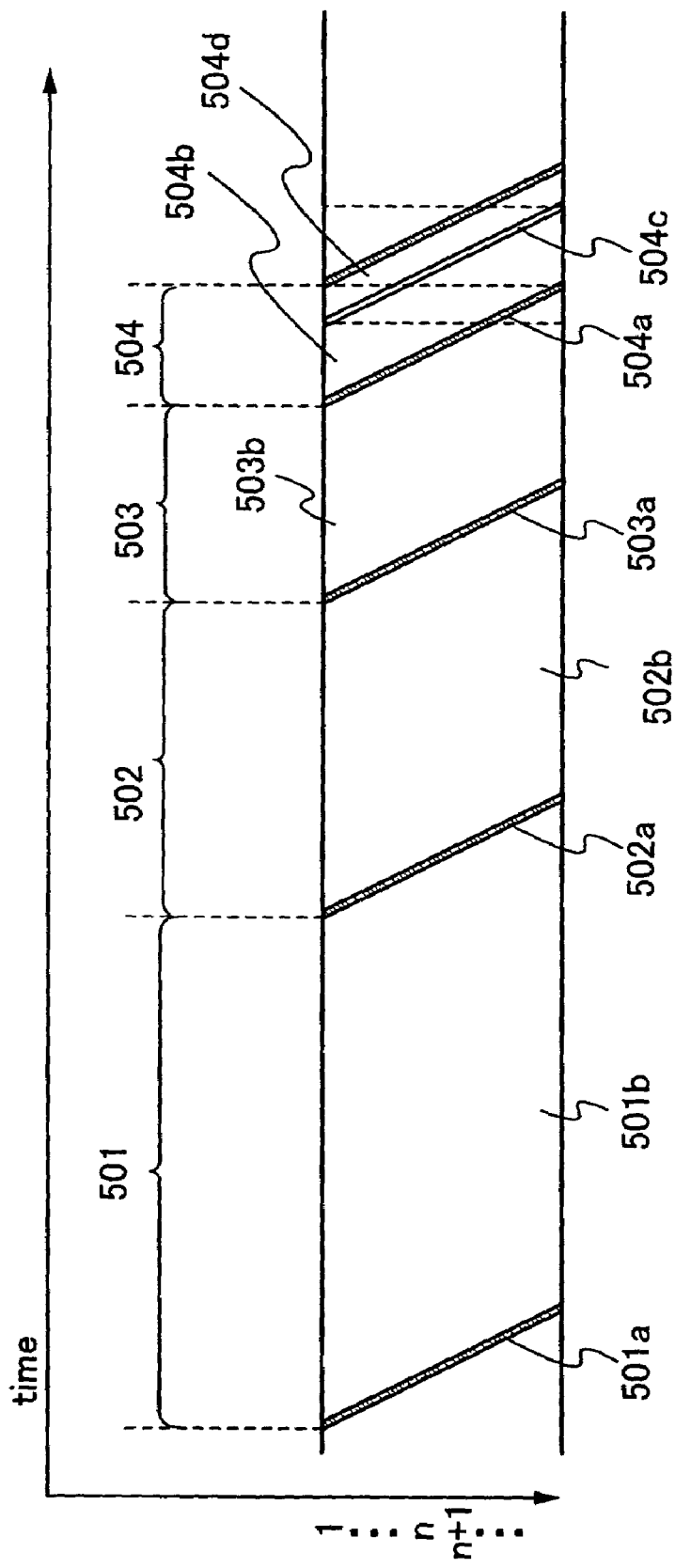
FIG. 6 is a diagram illustrating operation per frame for a light-emitting device according to the present invention after sealing.

Next, a driving method will be described. FIG. 6 is a diagram illustrating operation per frame with time. In FIG. 6, the lateral direction indicates passage of time, and the vertical direction indicates ordinal numbers of gate signal lines.

When a light-emitting device according to the present invention is used to display images, rewrite operation and image display operation for a screen are repeated in a display period. Although the number of rewrites is not particularly limited, it is preferable that the number of rewrites be about 60 times per second so as not to make an image viewer recognize flickers. Here, a period for which rewrite operation and display operation are performed for a screen (one frame) is referred to as one frame period.

As shown in FIG. 6, one frame is divided (time division) into four sub-frames 501, 502, 503, and 504 respectively including writing periods 501a, 502a, 503a, and 504a and retention periods 501b, 502b, 503b, and 504b. In the retention period, a light-emitting element to which a signal for emitting light is given is made to be in an emitting state. The ratio of the length of the retention period in each sub-frame is first sub-frame 501: second sub-frame 502: third sub-frame 503: fourth sub-frame $504 = 2^3:2^2:2^1:2^0 = 8:4:2:1$. This makes 4-bit gradation possible. However, the number of bits or the number of gradations is not limited to that described here. For example, eight sub-frames may be provided so as to perform 8-bit gradation.

Operation in one frame will be described. First, in the sub-frame 501, writing operation is sequentially performed for each of the first row to the last row. Accordingly, the start time of the writing period 501a is different depending on the row. When the writing period 501a is completed, the row is sequentially moved into the retention period 501b. In the retention period 501b, a light-emitting element to which a signal for emitting light is given is made to be in an emitting state. Further, when the retention period 501b is completed, the row is sequentially moved into the next sub-frame 502, and writing operation is sequentially performed for each of the first row to the last row as in the case of the sub-frame 501. The operation described above is repeated to complete the retention period 504b of the sub-frame 504. When the operation in the sub-frame 504 is completed, the row is moved into the next frame. Thus, the total of time for which light is emitted in each sub-frame is emission time for each light-emitting element in one frame. By varying this emission time with respect to each light-emitting element to have various combinations in one pixel, various different display colors in luminosity and chromaticity can be made.

As in the sub-frame 504, when forcible termination of a retention period of a row for which writing is already completed to move into the retention time is required before writing for the last row is completed, it is preferable that an erasing period 504c be provided after the retention period 504b and a row be controlled so as to be in a non-emitting state forcibly. Further, the row made to be in the non-emitting state forcibly is kept the non-emitting state for a certain period (this period is referred to as a non-emission period 504d). Then, immediately after the writing period 504a of the last row is completed, the rows are sequentially moved into the next writing period (or the next frame), starting from the first row. This makes it possible to prevent the writing period 504a of the sub-frame 504 from overlapping with the writing period of the next sub-frame.

Although the sub-frames 501 to 504 are arranged in the order of retention period from longest to shortest in the present embodiment, the arrangement as in the present embodiment is not always necessary. For example, the sub-frames 501 to 504 may be arranged in the order of retention period from shortest to longest, or may be arranged in random order. In addition, the sub-frames may be divided further into a plurality of frames. Namely, scanning of the gate signal lines may be performed more than once while giving the same image signal.

Now, operation of the circuit shown in FIG. 4 in a writing period and an erasing period will be described.

First, operation in a writing period will be described. In the writing period, the n-th (n is a natural number) gate signal line 911 is electrically connected to the gate signal line driver circuit 913 for writing through the switch 918, and unconnected to the gate signal line driver circuit 914 for erasing. In addition, the source signal line 912 is electrically connected to the source signal line driver circuit 915 through the switch 920. In this case, a signal is input to the gate of the first transistor 901 connected to the n-th (n is a natural number) gate signal line 911 to turn on the first transistor 901. Then, at this moment, image signals are input simultaneously to the first to last source signal lines 912. It is to be noted that the image signals input from the respective source signal lines 912 are independent of each other. The image signal input from each of the source signal lines 912 is input to the gate electrode of the second transistor 902 through the first transistor 901 connected to the source signal line 912. At this moment, the value of current to be supplied from the current supply line 917 to the light-emitting element 906 is determined in accordance with the signal input to the second transistor 902. Then, depending on the value of the current, whether the light-emitting element 903 emits light or not is determined. For example, when the second transistor 902 is a p-channel transistor, the light-emitting element 903 is made to emit light by inputting a Low Level signal to the gate electrode of the second transistor 902. On the other hand, when the second transistor 902 is an n-channel transistor, the light-emitting element 903 is made to emit light by inputting a High Level signal to the gate electrode of the second transistor 902.

Next, operation in an erasing period will be described. In the erasing period, the n-th (n is a natural number) gate signal line 911 is electrically connected to the gate signal line driver circuit 914 for erasing through the switch 919. In addition, the source signal line 912 is electrically connected to the power source 916 through the switch 920. In this case, a signal is input to the gate of the first transistor 901 connected to the n-th (n is a natural number) gate signal line 911 to turn on the first transistor 901. Then, at this moment, erasing signals are input simultaneously to the first to last source signal lines 912. The erasing signal input from each of the source signal lines 912 is input to the gate electrode of the second transistor 902 through the first transistor 901 connected to the source signal line 912. At this moment, current supply from the current supply line 917 to the light-emitting element 903 is blocked in accordance with the signal input to the second transistor 902. Then, the light-emitting element 903 is forcibly made to be in a non-emitting state. For example, when the second transistor 902 is a p-channel transistor, the light-emitting element 903 is made to emit no light by inputting a High Level signal to the gate electrode of the second transistor 902. On the other hand, when the second transistor 902 is an n-channel transistor, the light-emitting element 903 is made to emit no light by inputting a Low Level signal to the gate electrode of the second transistor 902.

It is to be noted that, as for the n-th row (n is a natural number), signals for erasing are input by the operation as described above in an erasing period. However, as described above, the other row (referred to as the m-th row (m is a natural number)) may be in a writing period while the n-th row is in an erasing period. In such a case, it is necessary to input a signal for erasing to the n-th row and input a signal for writing to the m-th row by using the same source signal line. Therefore, operation described below is preferable.

Immediately after the n-th light-emitting element 903 is made to emit no light by the operation in the erasing period described above, the gate signal line 911 and the gate signal line driver circuit 914 for erasing are made to be unconnected to each other, and the switch 920 is switched to connect the source signal line 912 and the source signal line driver circuit 915. Then, in addition to connecting the source signal line 912 to the source signal line driver circuit 915, the gate signal line 911 is connected to the gate signal line driver circuit 913 for writing. Then, a signal is input selectively to the m-th gate signal line 911 from the gate signal line driver circuit 913 for writing to turn on the first transistor 901, and signals for writing are input to the first to last source signal lines 912 from the source signal line driver circuit 915. This signal makes the m-th light-emitting element 903 is made to be in an emitting or non-emitting state.

Immediately after the writing period for the m-th row is completed as described above, an erasing period for the (n+1)-th row is started. For that purpose, the gate signal line 911 and the gate signal line driver circuit 913 for writing are made to be unconnected to each other, and the switch 920 is switched to connect the source signal line 912 and the power source 916. Further, the gate signal line 911, which is unconnected to the gate signal line driver circuit 913 for writing, is made to be connected to the gate signal line driver circuit 914 for erasing. Then, a signal is input selectively to the (n+1)-th gate signal line 911 from the gate signal line driver circuit 914 for erasing to turn on the first transistor 901, and an erasing signal is input from the power source 906. Immediately after the erasing period for the (n+1)-th row is completed, a writing period for the (m+1)-th row is started. Then, an erasing period and a writing period may be repeated in the same way until an erasing period for the last row is completed.

Although the example in which the writing period for the m-th row is provided between the erasing period for the n-th row and the erasing period for the (n+1)-th row is described in the present embodiment, the present invention is not limited to this. The writing period for the m-th row may be provided between an erasing period for (n−1)-th row and an erasing period for n-th row.

In addition, in the present embodiment, the operation in which the gate signal line driver circuit 914 for erasing and one gate signal line 911 are made to be unconnected to each other and the gate signal line driver circuit 913 for writing the other gate signal line 911 are made to be connected to each other is repeated as the non-emission period 504d is provided in the sub-frame 504. This type of operation may be performed in a frame in which a non-emission period is not provided.

EMBODIMENT 4

One example of a cross-sectional view of a light-emitting device including a light-emitting element according to the present invention will be described with reference to FIGS. 7A to 7C.

Figure 7A:
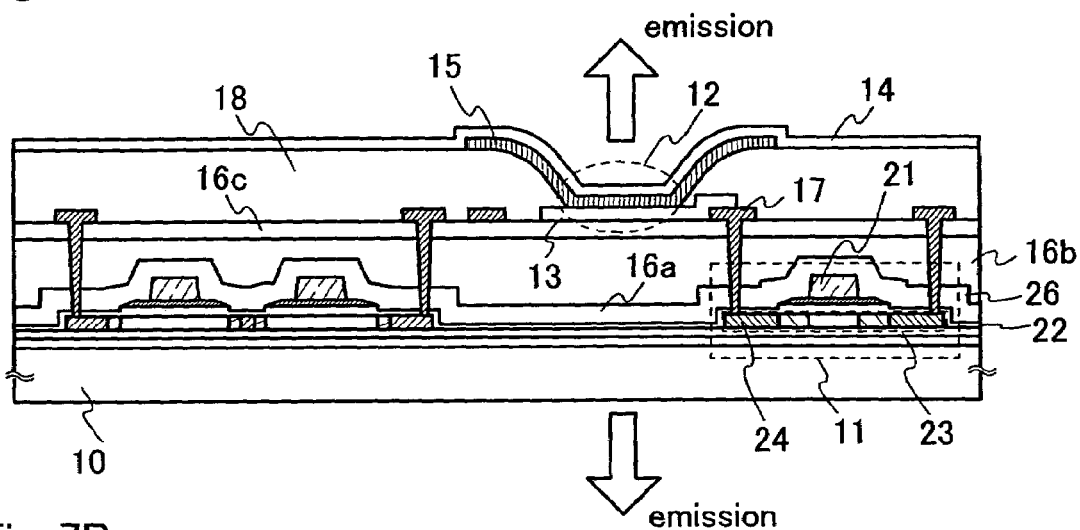
FIGS. 7A to 7C are cross-sectional views of light-emitting devices according to the present invention.
Figure 7B:
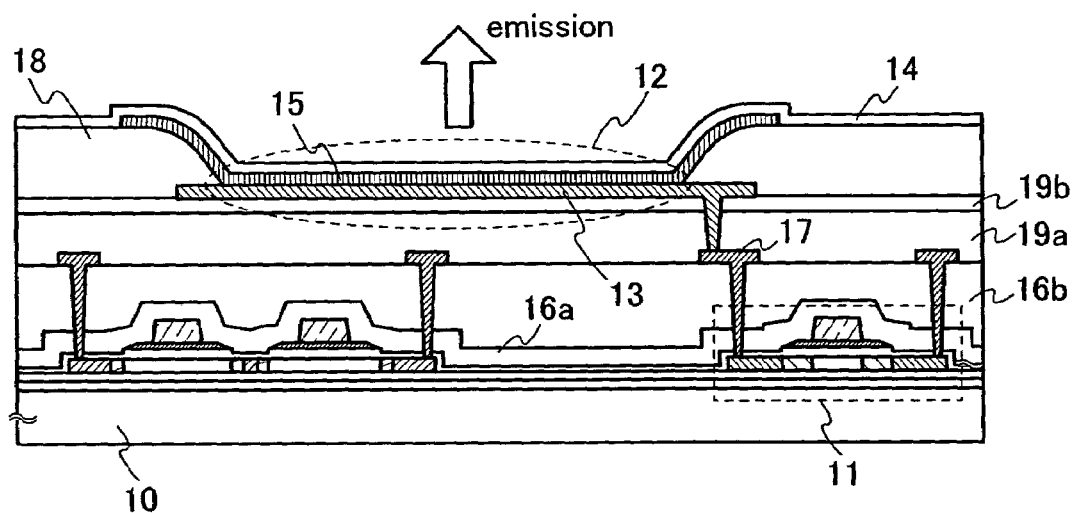
Figure 7C:
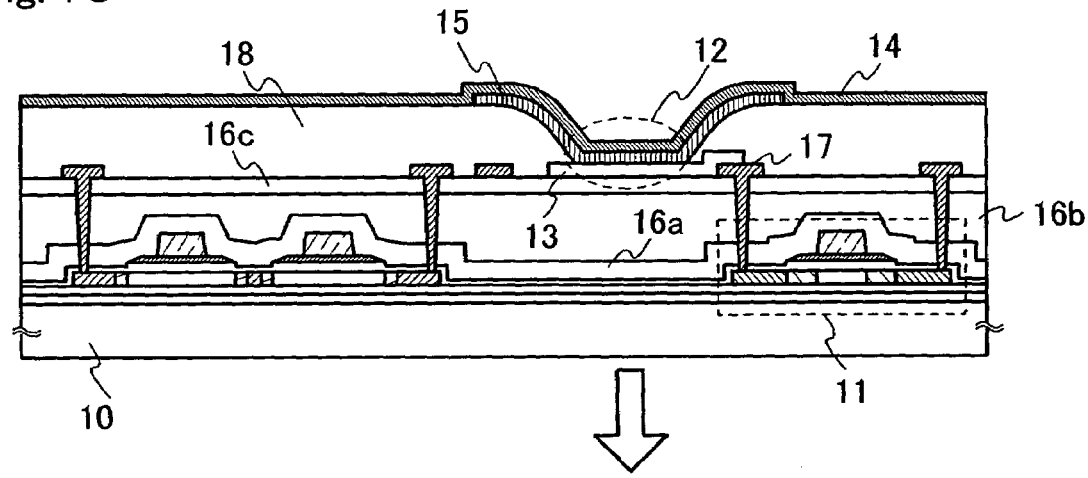

In each of FIGS. 7A to 7C, a portion surrounded by a dotted line is a transistor 11 provided for driving a light-emitting element 12 according to the present invention. The light-emitting element 12 is a light-emitting element according to the present invention, which has a light-emitting layer 15 between a first electrode 13 and a second electrode 14. The first electrode 13 and a drain of the transistor 11 are electrically connected to each other by a wiring 17 running through a first interlayer insulating film 16 (16a to 16c). In addition, the light-emitting element 12 is separated by a partition layer 18 from another light-emitting element provided adjacently. A light-emitting device that has this structure according to the present invention is provided over substrate 10.

The transistor 11 shown in each of FIGS. 7A to 7C is a top-gate TFT in which a gate electrode is provided over a semiconductor layer with a gate insulating film interposed therebetween. However, the structure of the transistor 11 is not particularly limited. For example, a bottom-gate TFT may be used. In the case of a bottom-gate TFT, a TFT where a protective film is formed on a semiconductor layer that forms a channel (a channel-protection TFT) may be used, or a TFT where a portion of a semiconductor layer that forms a channel is concave (a channel-etch TFT) may be used. Here, reference numerals 21, 22, 23, 24, 25, and 26 denote a gate electrode, a gate insulating film, a semiconductor layer, an n-type semiconductor layer, an electrode, and a protective film, respectively.

In addition, a semiconductor layer forming the transistor 11 may be either crystalline or amorphous, or alternatively, may be semi-amorphous.

The following will describe a semi-amorphous semiconductor. The semi-amorphous semiconductor is a semiconductor that has an intermediate structure between amorphous and crystalline (such as single-crystal or polycrystalline) structures and has a third state that is stable in terms of free energy, which includes a crystalline region that has short range order and lattice distortion. Further, a crystal grain from 0.5 to 20 nm is included in at least a region in a film of the semi-amorphous semiconductor. A raman spectrum of the semi-amorphous semiconductor has a shift to a lower wavenumber side than 520 $cm^{-1}$. In X-ray diffraction, diffraction peaks of (111) and (220) due to a Si crystal lattice are observed. Hydrogen or halogen is included at 1 atomic % or more in the semi-amorphous semiconductor to terminate a dangling bond. Therefore, the semi-amorphous semiconductor is also referred to as a micro-crystalline semiconductor. A nitride gas is decomposed by glow discharge (plasma CVD) to form the semi-amorphous semiconductor. As the nitride gas, in addition to $SiH_4$, a gas such as $Si_2H_6$, $SiH_2Cl_2$, $SiHCl_3$, $SiCl_4$, or $SiF_4$ can be used. This nitride gas may be diluted with $H_2$ or with $H_2$ and one kind or plural kinds of rare gas elements selected from He, Ar, Kr, and Ne, where the dilution ratio is in the range of 2:1 to 1000:1. The pressure during glow discharge is approximately in the range of 0.1 Pa to 133 Pa, and the power supply frequency is in the range of 1 MHz to 120 MHz, preferably 13 MHz to 60 MHz. The substrate heating temperature may be 300° C. or less, preferably 100 to 250° C.

It is desirable to control an impurity of an atmospheric constituent such as oxygen, nitrogen, or carbon to have a concentration of $1\times10^{20}$ /cm$^3$ or less as an impurity element in the film, in particular, the oxygen concentration is controlled to be $5\times10^{19}$/cm$^3$ or less, preferably $1\times10^{19}$/cm$^3$ or less.

Further, specific examples of crystalline semiconductors for the semiconductor layer include single-crystal or polycrystalline silicon and silicon-germanium, which may be formed by laser crystallization or may be formed by crystallization with solid-phase growth using an element such as nickel.

In the case of using an amorphous material, for example, amorphous silicon to form the semiconductor layer, it is preferable that the light-emitting device have a circuit in which the transistor 11 and the other transistor (a transistor forming the circuit for driving the light-emitting element) are all n-channel transistors. Other than that case, the light-emitting device may have a circuit including one of an n-channel transistor and a p-channel transistor or may have a circuit including both an n-channel transistor and a p-channel transistor.

Further, the first interlayer insulating film 16 may be a multilayer as shown in FIGS. 7A and 7C, or may be a single layer. The first interlayer insulating film 16a includes an inorganic material such as silicon oxide or silicon nitride, and the first interlayer insulating film 16b includes a material with self-flatness such as acrylic, siloxane (a material that has a framework structure formed by the bond between silicon (Si) and oxygen (O) and includes at least hydrogen in a substituent), silicon oxide that can be used in coating deposition. In addition, the first interlayer insulating film 16c has a silicon nitride film including argon (Ar). The materials included in the respective layers are not particularly limited, and therefore materials other than the materials mentioned here may be used. Further, a layer including a material other than these materials may be combined. In this way, both of an inorganic material and an organic material, or one of an inorganic material and an organic material may be used to form the first interlayer insulating film 16.

As for the partition layer 18, it is preferable that an edge portion have a shape varying continuously in curvature radius. In addition, a material such as acrylic, siloxane, resist, or silicon oxide is used to form the partition layer 18. One or both of an inorganic material and an organic material may be used to form the partition layer 18.

In each of FIGS. 7A and 7C, only the first interlayer insulating film 16 is provided between the transistor 11 and the light-emitting element 12. However, as shown in FIG. 7B, a second interlayer insulating film 19 (19a and 19b) may be provided in addition to the first interlayer insulating film 16 (16a and 16b). In the light-emitting device shown in FIG. 7B, the first electrode 13 is connected to the wiring 17 through the second interlayer insulating film 19.

The second interlayer insulating film 19 may be a multilayer or a single layer in the same way as the first interlayer insulating film 16. The second interlayer insulating film 19a includes a material with self-flatness such as acrylic, siloxane (a material that has a framework structure formed by the bond between silicon (Si) and oxygen (O) and includes at least hydrogen in a substituent), silicon oxide that can be used in coating deposition. In addition, the second interlayer insulating film 19b has a silicon nitride film including argon (Ar). The materials included in the respective layers are not particularly limited, and therefore materials other than the materials mentioned here may be used. Further, a layer including a material other than these materials may be combined. In this way, both of an inorganic material and an organic material, or one of an inorganic material and an organic material may be used to form the second interlayer insulating film 19.

In the light-emitting element 12, in the case where both of the first electrode 13 and the second electrode 14 are formed by using a light-transmitting material, emitted light can be extracted from both the first electrode 13 side and the second electrode 14 side as indicated by outline arrows of FIG. 7A. In the case where only the second electrode 14 is formed by using a light-transmitting material, emitted light can be extracted from only the second electrode 14 side as indicated by an outline arrow of FIG. 7B. In this case, it is preferable that the first electrode 13 include a highly reflective material or that a film composed of a highly reflective material (a reflective film) be provided below the first electrode 13. In the case where only the first electrode 13 is formed by using a light-transmitting material, emitted light can be extracted from only the first electrode 13 side as indicated by an outline arrow of FIG. 7C. In this case, it is preferable that the second electrode 14 include a highly reflective material or that a reflective film is provided above the second electrode 14.

In addition, in the case of the light-emitting element 12, the first electrode 13 may function as an anode while the second electrode 14 functions as a cathode, or alternatively, the first electrode 13 may function as a cathode while the second electrode 14 functions as an anode. However, the transistor 11 is a p-channel transistor in the former case, and the transistor 11 is an n-channel transistor in the latter case.

EMBODIMENT 5

By mounting a light-emitting device according to the present invention, an electronic device that is capable of favorable displays for a long period or an electric appliance that is capable of favorable lighting for a long period can be obtained.

Figure 8A:
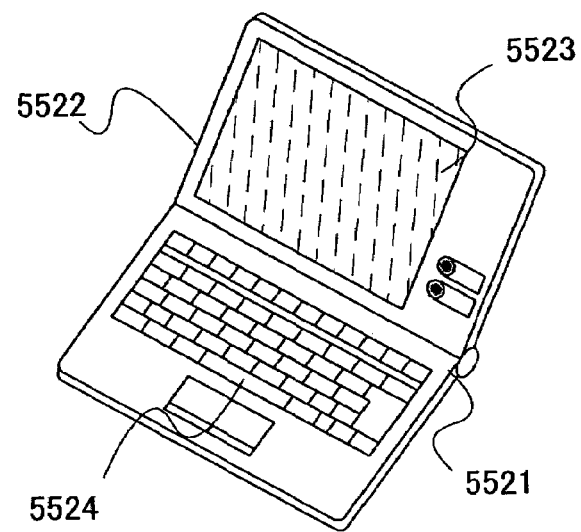
FIGS. 8A to 8C are diagrams of electronic devices according to the present invention.
Figure 8B:
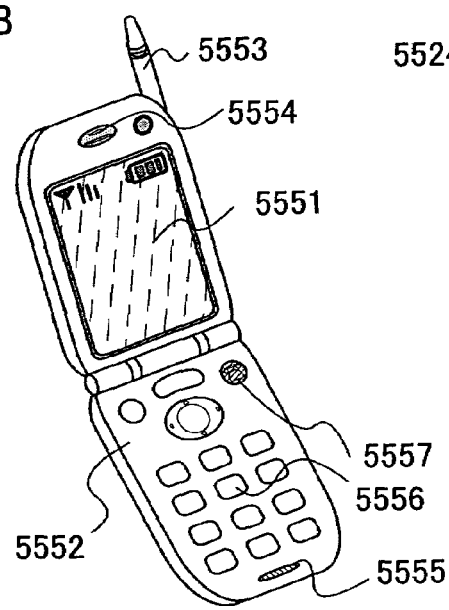
Figure 8C:
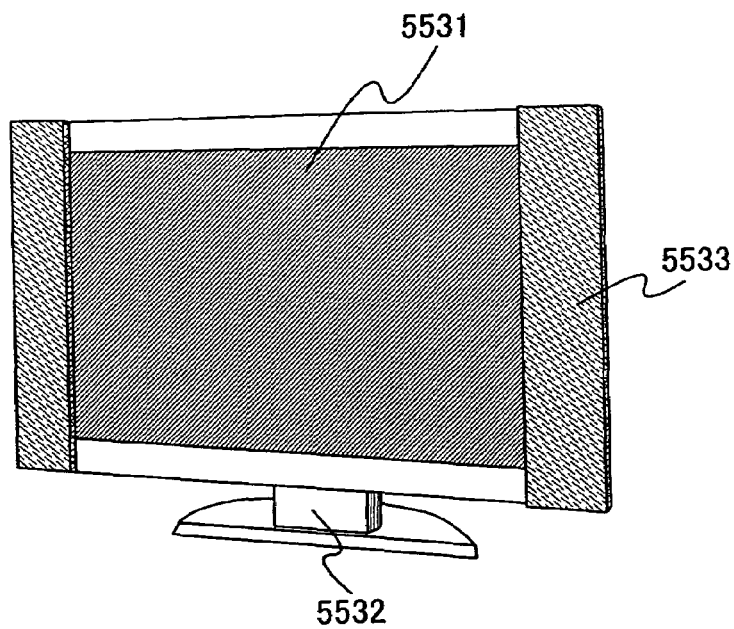

FIGS. 8A to 8C show examples of an electronic device mounted with a light-emitting device to which the present invention is applied.

FIG. 8A shows a laptop personal computer manufactured according to the present invention, which includes a main body 5521, a frame body 5522, a display portion 5523, and a keyboard 5524. The personal computer can be completed by incorporating a light-emitting device that has a light-emitting element according to the present invention in the display portion 5523.

FIG. 8B shows a cellular phone manufactured according to the present invention, which includes a main body 5552, a display portion 5551, a voice output portion 5554, a voice input portion 5555, operation keys 5556 and 5557, and an antenna 5553. The cellular phone can be completed by incorporating a light-emitting device that has a light-emitting element according to the present invention into the display portion 5551.

FIG. 8C shows a television manufactured according to the present invention, which includes a display portion 5531, a frame body 5532, and a speaker 5533. The television can be completed by incorporating a light-emitting device that has a light-emitting element according to the present invention into the display portion 5531.

As described above, a light-emitting device according to the present invention is suitable for use as display portions of various electronic devices.

In the present embodiment, the laptop personal computer, the cellular phone, and the television are described. However, in addition, a light-emitting device that has a light-emitting element according to the present invention may be mounted in devices such as a car navigation system and a lighting apparatus.

EXAMPLE 1

SYNTHESIS EXAMPLE

[Step 1]

A synthesis method of 9,10-bis(4-bromophenyl)-2-tert-butylanthracene will be described.

Under a nitrogen flow, at −78° C., a 1.58 N hexane solution of butyllithium (13.4 mL) was dropped in a dry ether solution (200 mL) of p-dibromobenzene (5.0 g). After completion of the dropping, stirring was carried out at the same temperature (−78° C.). A dry ether solution (40 mL) of 2-t-butylanthraquinone (2.80 g) was dropped at −78° C., and then the reaction solution was slowly raised to room temperature. After overnight stirring at room temperature, water was added, and extraction was carried out with ethyl acetate. The organic layer was washed with a saturated aqueous solution of sodium chloride, dried with magnesium sulfate, filtered, and condensed. Then, the residue was purified by silica gel chromatography (developing solvent, hexane-ethyl acetate) to obtain a compound (5.5 g).

Measurement of the obtained compound by nuclear magnetic resonance ($^1$H-NMR) could confirm that the compound was 9,10-bis(4-bromophenyl)-2-tert-butyl-9,10-dihydroxy-9,10-dihydroanthracene.

$^1$H-NMR data of this compound is shown below.

$^1$H-NMR (300 MHz, CDCl$_3$); δ=1.31 (s, 9H), 2.81 (s, 1H), 2.86 (s, 1H), 6.82-6.86 (m, 4H), 7.13-7.16 (m, 4H), 7.36-7.43 (m, 3H), 7.53-7.70 (m, 4H)

In addition, the synthesis scheme (b-1) of 9,10-bis(4-bromophenyl)-2-tert-butyl-9,10-dihydroxy-9,10-dihydroanthracene is shown below.

9,10-dihydroanthracene, 664 mg (4 mmol) of potassium iodide, and 1.48 g (14 mmol) of sodium phosphinate dehydrate were suspended in 14 mL of glacial acetic acid, and held at reflux for 2 hours while heating and stirring. After cooling to room temperature, a produced precipitation was filtered, and washed with about 50 mL of methanol to obtain a filtered object. Then, the filtered object was dried to obtain a cream powdery compound (700 mg). The yield was 82%. Measurement of this compound by nuclear magnetic resonance ($^1$H-NMR and $^{13}$C-NMR) could confirm that the compound was 9,10-bis(4-bromophenyl)-2-tert-butylanthracene.

$^1$H-NMR data and $^{13}$C-NMR data of this compound is shown below. $^1$H-NMR (300 MHz, CDCl$_3$); δ=1.28 (s, 9H), 7.25-7.37 (m, 6H), 7.44-7.48 (m, 1H), 7.56-7.65(m, 4H), 7.71-7.76 (m, 4H)

$^{13}$C-NMR (74 MHz, CDCl$_3$); δ=30.8, 35.0, 120.8, 121.7, 121.7, 124.9, 125.0, 125.2, 126.4, 126.6, 126.6, 128.3, 129.4, 129.7, 129.9, 131.6, 131.6, 133.0, 133.0, 135.5, 135.7, 138.0, 138.1, 147.8

In addition, the synthesis scheme (b-2) of 9,10-bis(4-bromophenyl)-2-tert-butylanthracene is shown below.

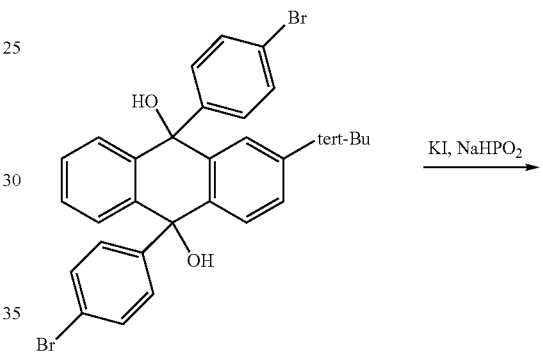

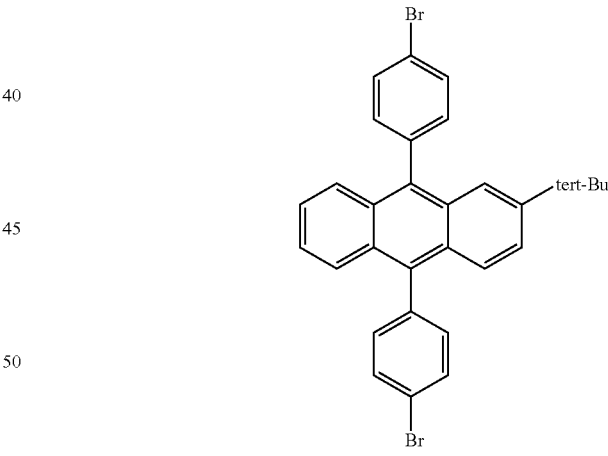

(b-2)

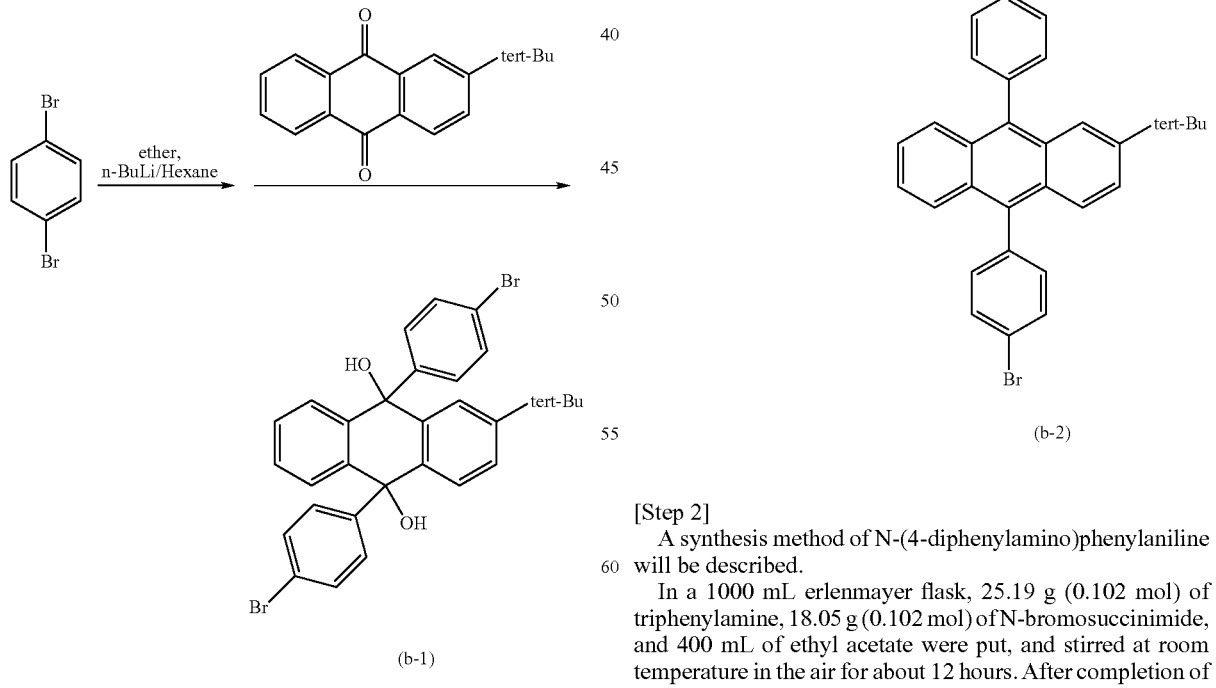

(b-1)

In the atmosphere, 987 mg (1.55 mmol) of the thus synthesized 9,10-bis(4-bromophenyl)-2-tert-butyl-9,10-dihydroxy-

[Step 2]

A synthesis method of N-(4-diphenylamino)phenylaniline will be described.

In a 1000 mL erlenmayer flask, 25.19 g (0.102 mol) of triphenylamine, 18.05 g (0.102 mol) of N-bromosuccinimide, and 400 mL of ethyl acetate were put, and stirred at room temperature in the air for about 12 hours. After completion of the reaction, the organic layer was washed twice with a saturated aqueous solution of sodium carbonate, then, the aqueous layer was subjected to extraction twice with ethyl acetate, and the ethyl acetate layer mixed with the organic layer was washed with a saturated aqueous solution of sodium chloride. After drying with magnesium sulfate, natural filtration, and condensation, the obtained colorless solid was recrystallized with ethyl acetate and hexane to obtain a colorless powdery solid (22.01 g, yield: 66%). Nuclear magnetic resonance ($^1$H-NMR) could confirm that this colorless powdery solid was 4-bromotriphenylamine. The measurement result by nuclear magnetic resonance (NMR) is shown below.

$^1$H-NMR data of this compound is shown below.

$^1$H-NMR (300 MHz, CDCl$_3$) δ ppm: 7.32 (d, 2H, J=8.7 Hz), 7.29-7.23 (m, 4H), 7.08-7.00 (m, 6H), 6.94 (d, 2H, J=8.7 Hz)

In addition, the synthesis scheme (c-1) of 4-bromotriphenylamine is shown below.

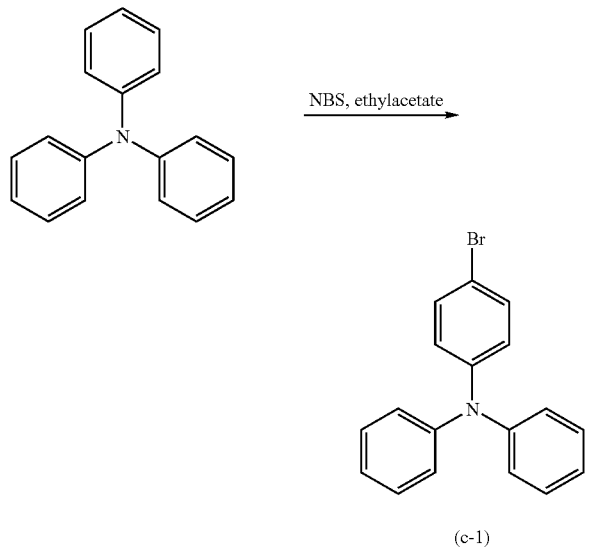

Next, 7.21 g (0.053 mol) of acetoanilide, 17.32 g (0.053 mol) of the synthesized 4-bromotriphenylamine, 2.05 g (0.011 mol) of copper (I) iodide, and 22.00 g (0.103 mol) of tripotassium phosphate were put in a 500 mL three-neck flask, and the atmosphere in the flask was made a nitrogen atmosphere. Then, 150 mL of dioxane and 1.3 mL of trans-1,2-cyclohexanediamine were added, and reflux for 40 hours was carried out. After completion of the reaction, the solid in the flask was removed by suction filtration after cooling to room temperature. The filtrate was washed twice with a saturated aqueous solution of sodium carbonate, the aqueous layer was subjected to extraction twice with chloroform, and the chloroformlayer mixed with the organic layer was washed with a saturated aqueous solution of sodium chloride. After drying with magnesium sulfate, natural filtration, and condensation, the obtained white solid was purified by silica gel chromatography (ethyl acetate: hexane=1:1) to obtain a white powdery solid (12.00 g, yield: 59%). Nuclear magnetic resonance ($^1$H-NMR) could confirm that this white powdery solid was N-(4-diphenylamino) phenylacetoanilide.

$^1$H-NMR data of this compound is shown below.

$^1$H-NMR (300 MHz, CDCl$_3$) δ ppm:7.36-7.23 (m, 9H), 7.12-7.03 (m, 10H), 2.07 (s, 3H)

In addition, the synthesis scheme (c-2) of N-(4-diphenylamino)phenylacetoanilide is shown below.

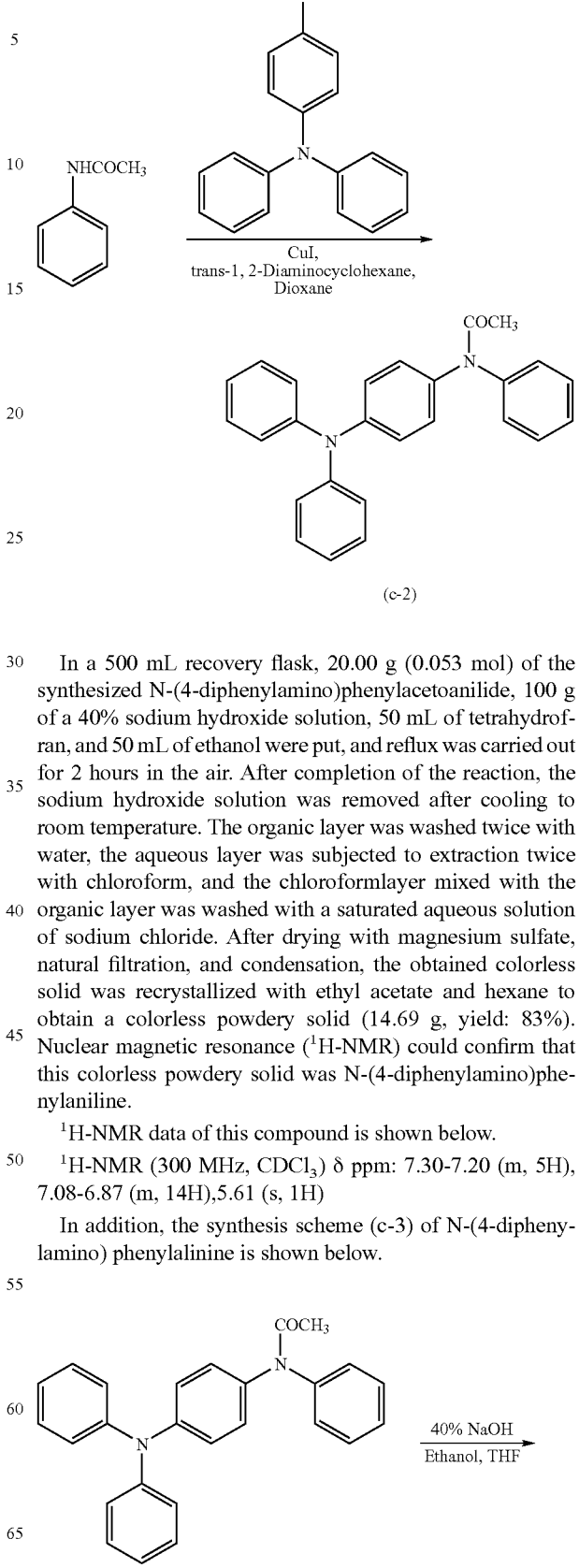

In a 500 mL recovery flask, 20.00 g (0.053 mol) of the synthesized N-(4-diphenylamino)phenylacetoanilide, 100 g of a 40% sodium hydroxide solution, 50 mL of tetrahydrofuran, and 50 mL of ethanol were put, and reflux was carried out for 2 hours in the air. After completion of the reaction, the sodium hydroxide solution was removed after cooling to room temperature. The organic layer was washed twice with water, the aqueous layer was subjected to extraction twice with chloroform, and the chloroformlayer mixed with the organic layer was washed with a saturated aqueous solution of sodium chloride. After drying with magnesium sulfate, natural filtration, and condensation, the obtained colorless solid was recrystallized with ethyl acetate and hexane to obtain a colorless powdery solid (14.69 g, yield: 83%). Nuclear magnetic resonance ($^1$H-NMR) could confirm that this colorless powdery solid was N-(4-diphenylamino)phenylaniline.

$^1$H-NMR data of this compound is shown below.

$^1$H-NMR (300 MHz, CDCl$_3$) δ ppm: 7.30-7.20 (m, 5H), 7.08-6.87 (m, 14H),5.61 (s, 1H)

In addition, the synthesis scheme (c-3) of N-(4-diphenylamino) phenylalinine is shown below.

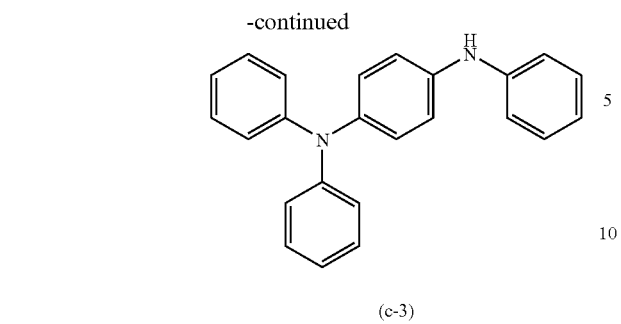

(c-3)

[Step 3]

A synthesis method of 9,10-bis{4-[N-(4-diphenylamino)phenyl-N -phenyl]aminophenyl}-2-tert-butylanthracene represented by the structure formula (6) will be described.

In a 200 mL three-neck flask, 2.00 g (0.0037 mol) of 9,10-bis(4-bromophenyl)-2-tert-butylanthracene, 2.61 g (0.0078 mol) of N-(4-diphenylamino)phenylalinine, 428 mg (0.77 mmol) of bis(dibenzylideneacetone)palladium(0), and 2.00 g (0.021 mol) of sodium t-butoxide were put, and the atmosphere within the flask was made to be under a nitrogen flow. After that, 20 mL of dehydrated toluene and 4.0 mL of a 10% hexane solution of tri -tert-butylphosphine were added, and stirring was carried out at 80° C. for 8 hours. After completion of the reaction, the reaction solution was cooled to room temperature and washed twice with water, the aqueous layer was subjected to extraction twice with chloroform, and the chloroformlayer mixed with the organic layer was washed with a saturated aqueous solution of sodium chloride and dried with magnesium sulfate. After natural filtration and condensation, the obtained brown oily object was purified by silica gel chromatography (hexane:ethyl acetate=9:1) and then recrystallized with ethyl acetate and hexane to obtain a yellow powdery solid (1.14 g, yield: 29%, refer to a synthesis scheme (d-1)). Nuclear magnetic resonance ($^1$H-NMR) could confirm that this yellow powdery solid was 9,10-bis{4-[N-(4-diphenylamino)phenyl-N -phenyl]aminophenyl}-2-tert-butylanthracene (abbreviation: DPABPA).

$^1$H-NMR data of this compound is shown below.

$^1$H-NMR (300 MHz, CDCl$_3$) δ ppm: 7.89-7.81 (m, 2H), 7.78 (d, 1H, J=9.3 Hz), 7.66 (d, 2H, J=1.8 Hz), 7.48 (d, d, 1H, J=9.3 Hz), 7.38-7.24 (m, 25H), 7.17-7.13 (m, 12H), 7.08-6.98 (m, 10H), 1.30 (s, 9H)

In addition, the synthesis scheme (d-1) of DPABPA is shown below.

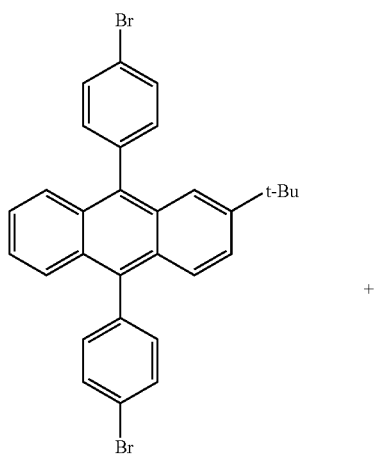

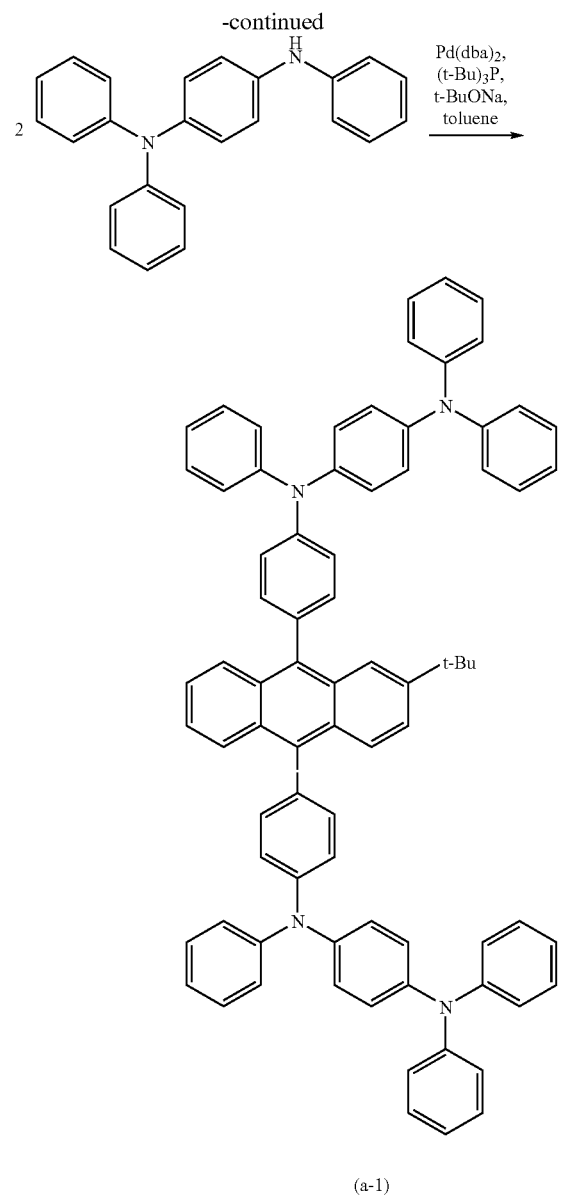

(a-1)

Figure 9:
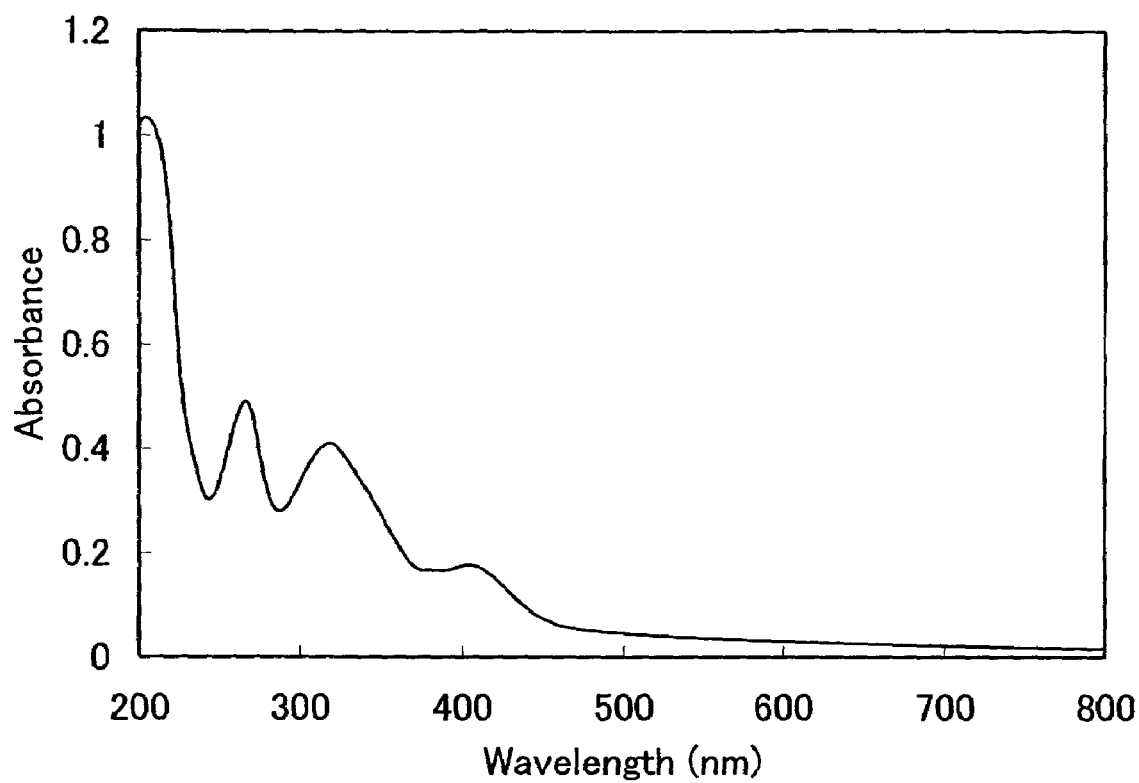
FIG. 9 is a diagram showing an absorption spectrum of a single film of an anthracene derivative according to the present invention.
Figure 10:
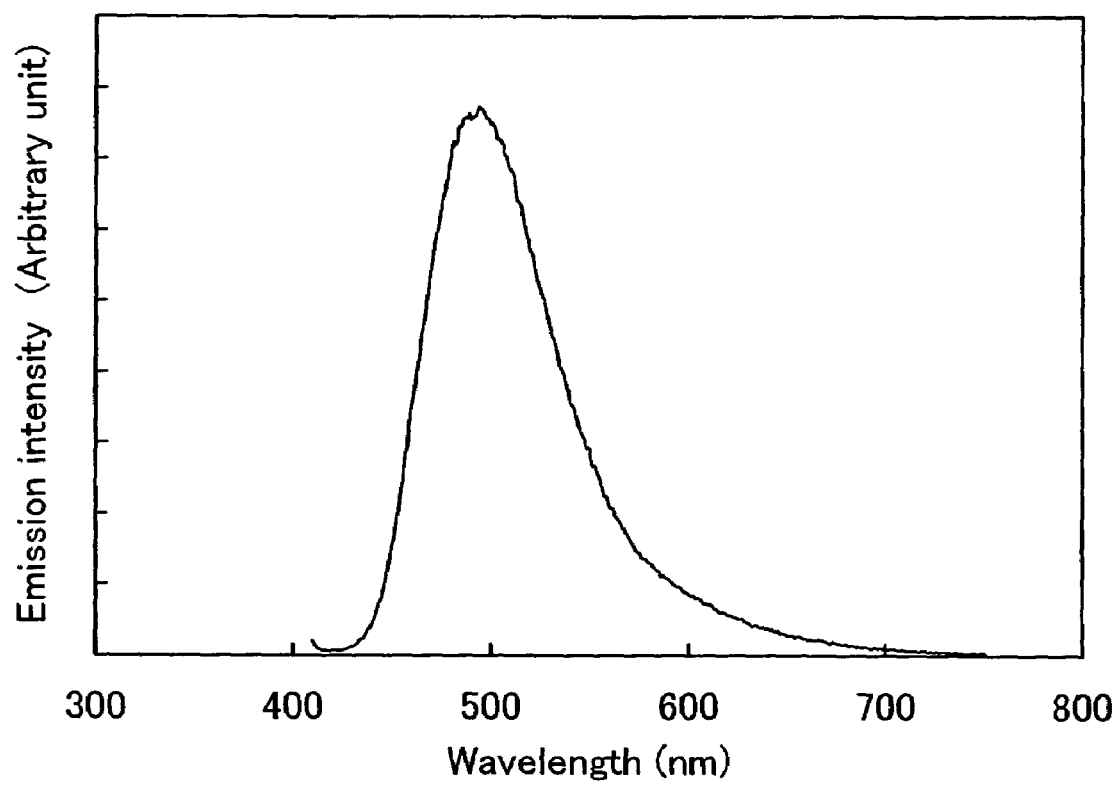
FIG. 10 is a diagram showing an emission spectrum of the single film of the anthracene derivative according to the present invention.

Further, FIG. 9 shows an absorption spectrum of a single film of DPABPA. In FIG. 9, the horizontal axis indicates a wavelength (nm), and the vertical axis indicates an absorbance (without a unit). In addition, FIG. 10 shows an emission spectrum of the single film of DPABPA excited at 403 nm. In FIG. 10, the horizontal axis indicates a wavelength (nm), and the vertical axis indicates emission intensity (arbitrary unit). From FIG. 10, it is determined that the single film of DPABPA shows blue or bluish luminescence with a peak at 494 nm.

Further, the stability of DPABPA against oxidation was examined by cyclic voltammetry (CV). It is to be noted that an electrochemical analyzer (ALS, Model 600A) from BAS was used for the measurement.

In the CV measurement, tetra-n-butylammonium perchlorate (n-Bu$_4$NClO$_4$) and dimethylformamide (DNF) were used as a supporting electrolyte and a solvent, respectively. In addition, a Pt electrode, a Pt electrode, and a Ag/Ag$^+$ electrode were used as a work electrode, an auxiliary electrode, and a reference electrode, respectively. The scan rate in the CV measurement is controlled to be 0.025 V/s, and a series of operations as one cycle, scanning for changing the potential of the work electrode with respect to the Ag/Ag$^+$ from 0 to 0.4 V and scanning for returning the potential from 0.4 to 0 V, was performed repeatedly to complete 500 cycles.

Figure 11:
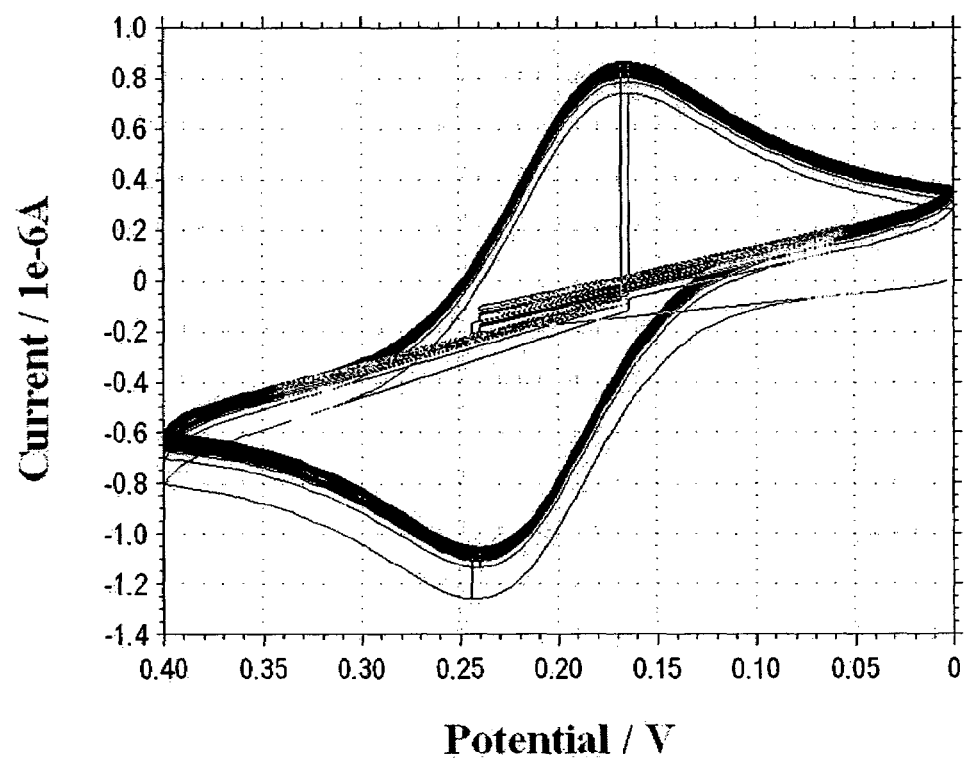
FIG. 11 is a diagram showing a measurement result of the anthracene derivative according to the present invention by cyclic voltammetry (CV)

The result is shown in FIG. 11. It is to be noted that the horizontal axis and the vertical axis respectively indicate a potential (V) with respect to the Ag/Ag$^+$ electrode and a current value (A) in FIG. 11. From FIG. 11, it is determined that the oxidation potential is 24 V (vs. Ag/Ag$^+$ electrode). In addition, there is almost no variation in peak position or peak intensity of the CV curve in FIG. 11 in spite of the repeated 500 cycles of operations. From this result, it is determined that DPABPA according to the present invention is quite stable against oxidation.

EXAMPLE 2

Figure 2:
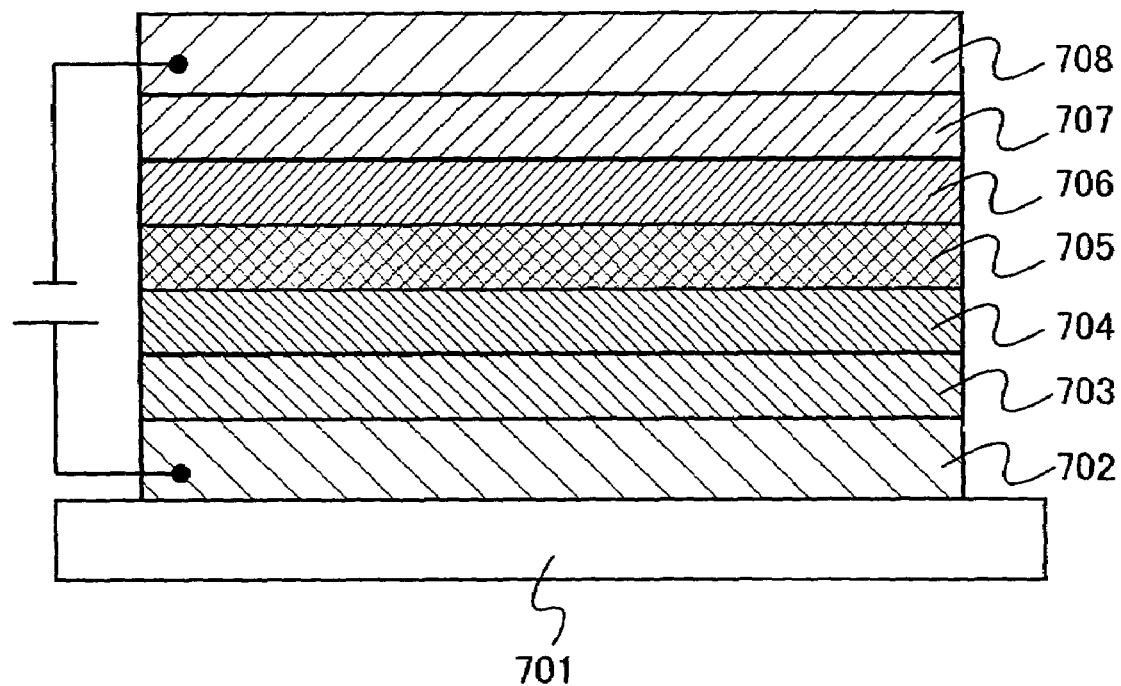
FIG. 2 is a diagram illustrating a light-emitting device according to the present invention.

In the present example, an example of manufacturing a light-emitting element using 9,10-bis[4-(N-(4-diphenylamino)phenyl-N-phenyl) aminophenyl]-2-tert-butylanthracene(abbreviation: DPABPA) represented by the structure formula (6) will be described with reference to FIG. 2.

On a glass substrate 701, indium tin oxide containing silicon was deposited by sputtering to form a first electrode 702. The film thickness thereof was made to be 110 nm.

Next, on the first electrode 702, DNTPD was deposited by vacuum evaporation to form a layer 703 including DNTPD. The film thickness thereof was made to be 30 nm.

Next, on the layer 703 including DNTPD, α-NPD was deposited by vacuum evaporation to form a layer 704 including α-NPD. The film thickness thereof was made to be 30 nm.

Next, on the layer 704 including α-NPD, t-BuDNA and DPABPA represented by the structure formula (6) were deposited by co-evaporation to form a layer 705 including t-BuDNA and DPABPA. The layer 705 was made to include t-BuDNA at 95 weight % and DPABPA at 5 weight %. This makes DPABPA dispersed as guest material in t-BuDNA as host material. In addition, the film thickness of the layer 705 was made to be 40 nm. It is to be noted that co-evaporation is an evaporation method in which evaporation is performed simultaneously from a plurality of evaporation sources.

Next, on the layer 705 including t-BuDNA and DPABPA, Alq$_3$ was deposited by vacuum evaporation to form a layer 706 including Alq$_3$. The film thickness thereof was made to be 20 nm.

Next, on the layer 706 including Alq$_3$, calcium fluoride was deposited by vacuum evaporation to form a layer 707 including calcium fluoride. The film thickness thereof was made to be 1 nm.

Next, on the layer 707 including calcium fluoride, aluminum was deposited by vacuum evaporation to form a second electrode 708.

By manufacturing a light-emitting element as described above, it is possible to obtain a light-emitting element from which luminescence from DPABPA can be obtained.

In the thus manufactured light-emitting element, when a voltage is applied to the first electrode 702 and the second electrode 708 to flow current, DPABPA produces luminescence. In this case, the first electrode 702 serves as an anode and the second electrode 708 serves as a cathode. In addition, the layer 703 including DNTPD, the layer 704 including α-NPD, the layer 705 including t-BuDNA and DPABPA, the layer 706 including Alq$_3$, and the 707 including calcium fluoride serve as a hole injecting layer, a hole transporting layer, a light-emitting layer, an electron transporting layer, and an electron injecting layer, respectively.

Further, sealing of the light-emitting element manufactured as described above was performed. It is to be noted that the sealing was performed in a nitrogen atmosphere in a glove box.

Then, the light-emitting element after the sealing was driven to examine current density-luminance characteristics, voltage-luminance characteristics, and luminance-current efficiency characteristics in an initial condition. It is to be noted that the measurement was performed in an atmosphere kept at 25° C.

Figure 12:
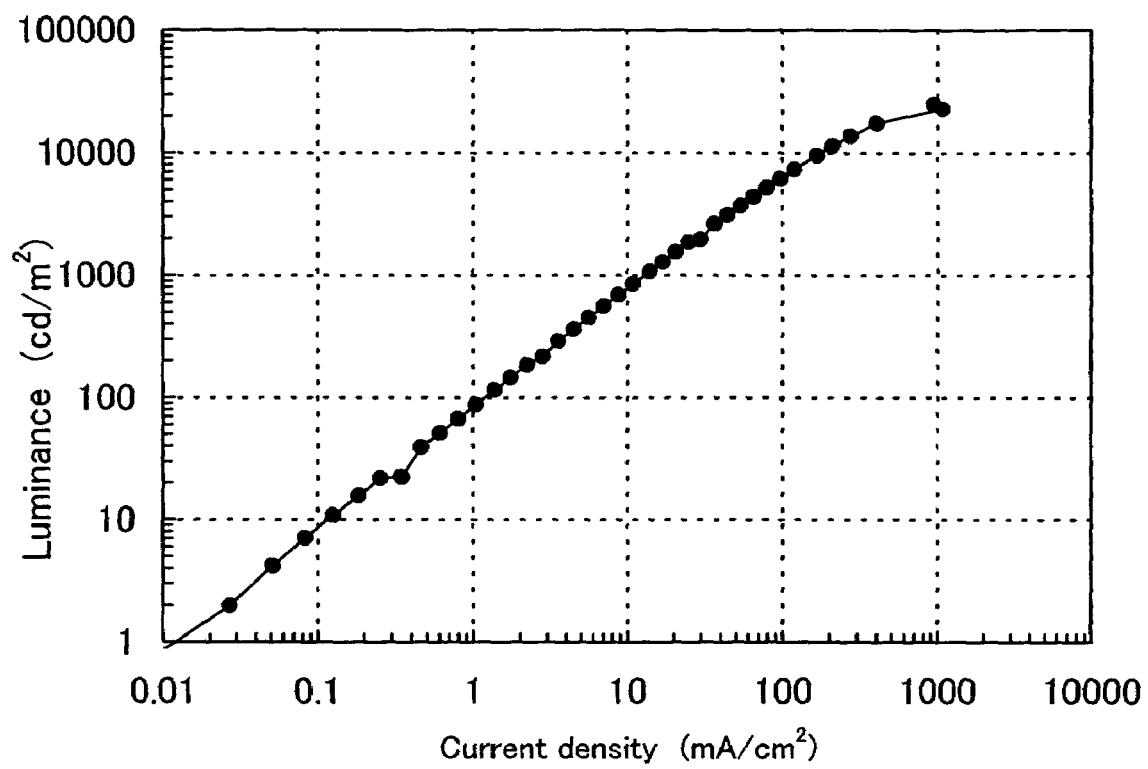
FIG. 12 is a diagram showing current density-luminance characteristics of a light-emitting element according to the present invention.
Figure 13:
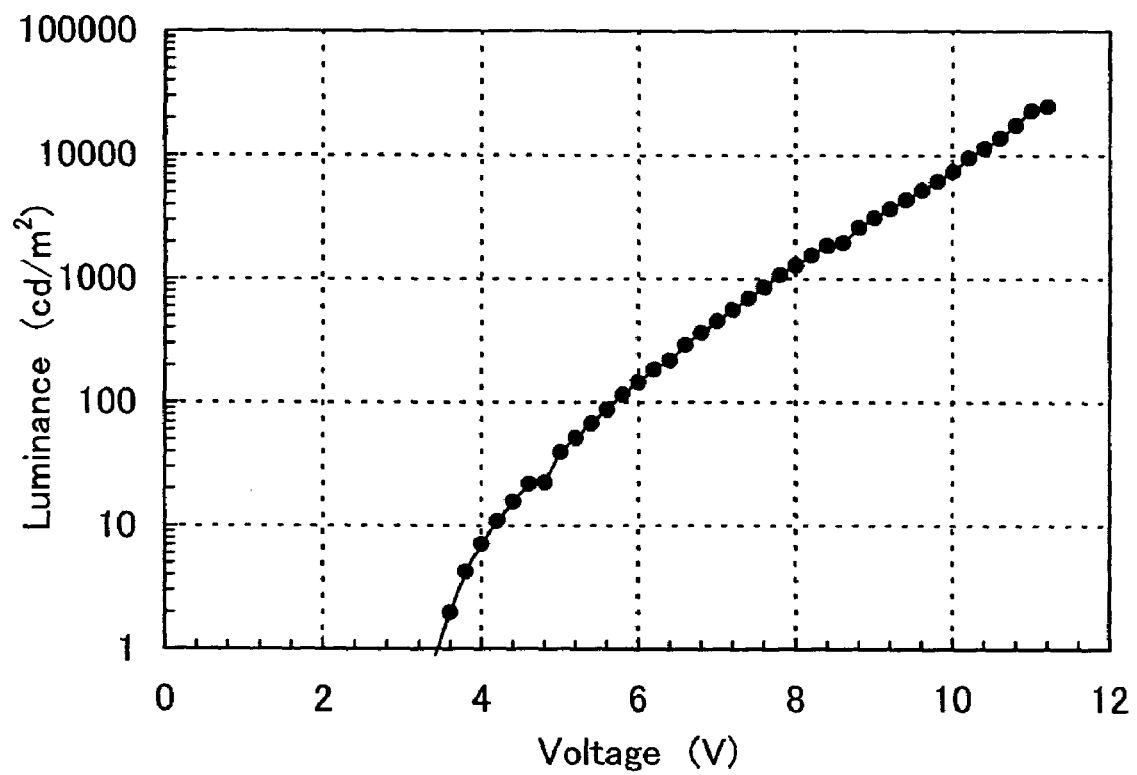
FIG. 13 is a diagram showing voltage-luminance characteristics of the light-emitting element according to the present invention.
Figure 14:
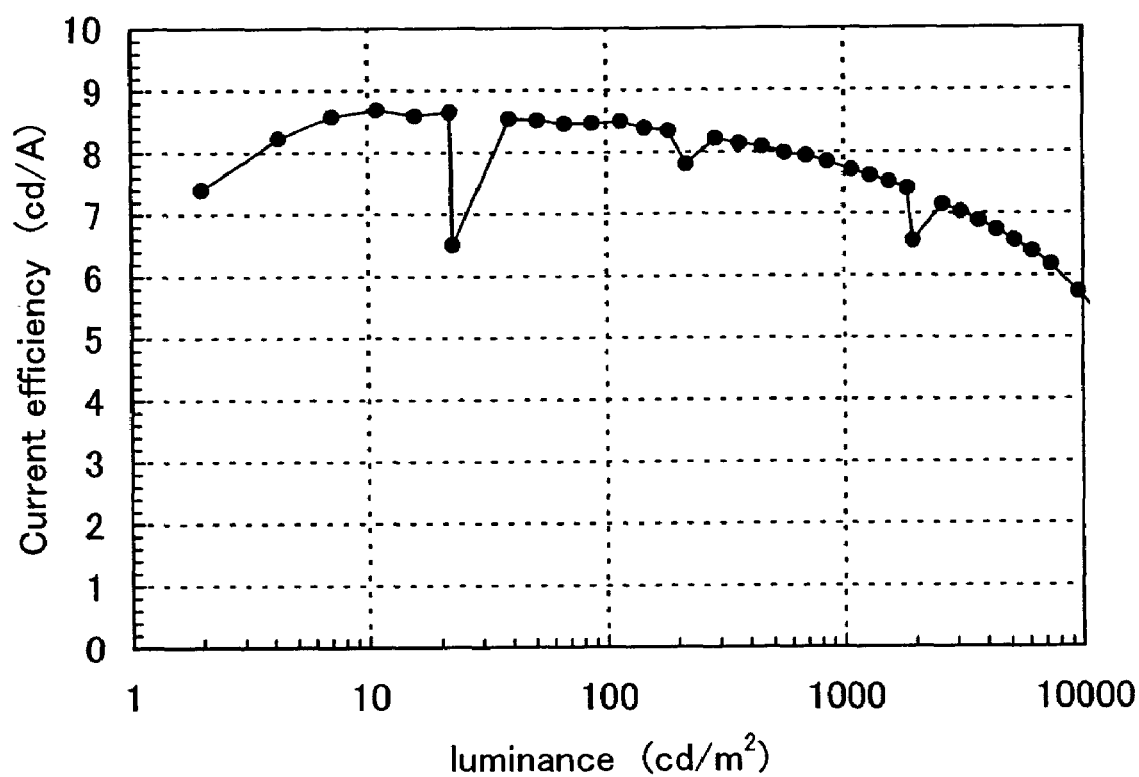
FIG. 14 is a diagram showing luminance-current efficiency characteristics of the light-emitting element according to the present invention.

FIGS. 12, 13, 14 respectively show current density-luminance characteristics, voltage-luminance characteristics, and luminance-current efficiency characteristics. In FIG. 12, the horizontal axis indicates a current density, and the vertical axis indicates a luminance. In FIG. 13, the horizontal axis indicates a voltage, and the vertical axis indicates a luminance. In FIG. 14, the horizontal axis indicates a luminance, and the vertical axis indicates a current efficiency.

From the voltage-luminance characteristics in FIG. 13, it is determined that the light-emitting element in the present example emitted light with a luminance of 290 cd/m$^2$ when a voltage of 6.6 V was applied. In addition, it is determined that the luminance efficiency was 8.2 cd/A when the voltage of 6.6 V was applied.

Further, an emission spectrum of the light-emitting element had a peak at 486 nm, and the CIE chromaticity coordinates were (x, y)=(0.19, 0.37).

For the light-emitting element in the present invention, which has the initial performance described above, an operational stability test by constant current driving was performed. A current of a current density (3.54 mA/cm$^2$) required for emitting light with a luminance of 290 cd/m$^2$ in the initial condition was kept flowed for a certain period of time to examine change in luminance with time. In the result, it was determined that the luminance after a lapse of 600 hours was 86% of the luminance in the initial condition. From this result, it is determined that the light-emitting element according to the present invention is small reduced in luminance with time, and has a favorable life.

Figure 15:
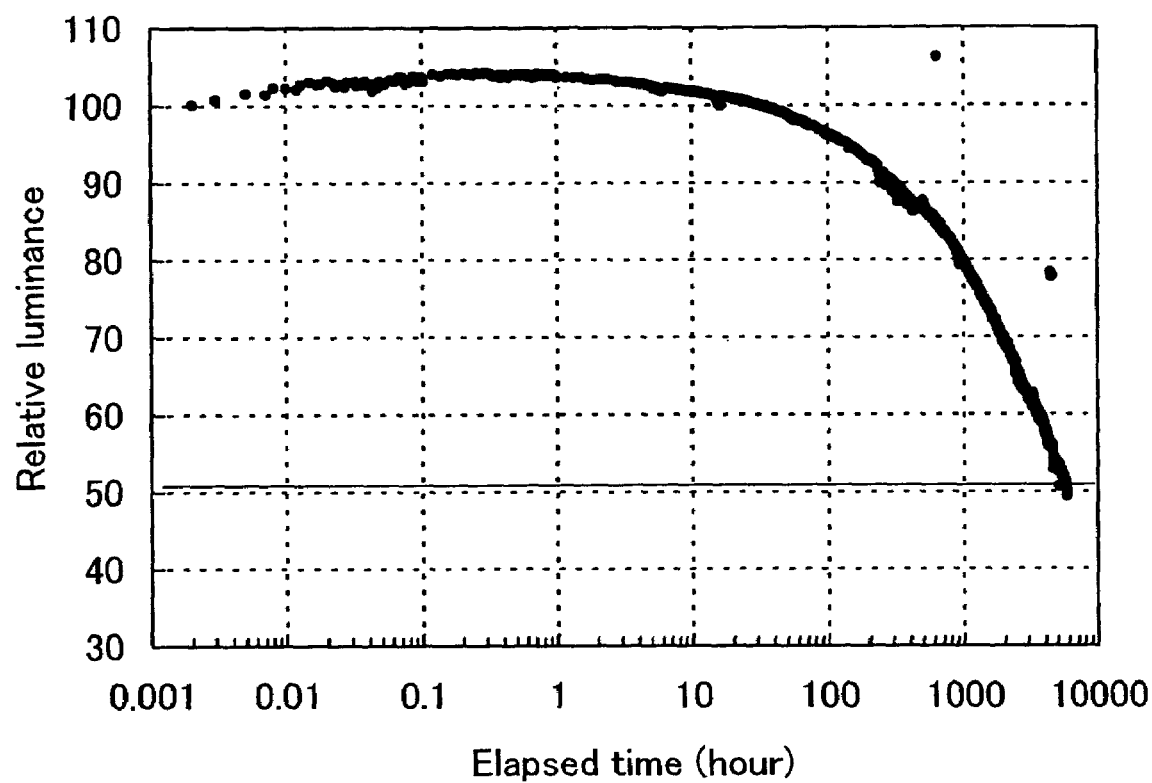
FIG. 15 is a diagram showing a measurement result of the light-emitting element according to the present invention by performing an operational stability test.

FIG. 15 shows the measurement result of the operational stability test. In FIG. 15, the horizontal axis indicates elapsed time (hour) since the initial state, and the vertical axis indicates a relative luminance (arbitrary unit) with respect to the initial luminance when the initial luminance is indicated as 100.

Although the present invention has been fully described by way of example with reference to the accompanying drawings, it is to be understood that various changes and modifications will be apparent to those skilled in the art. Therefore, unless such changes and modifications depart from the scope of the present invention hereinafter defined, they should be construed as being included therein.

What is claimed is:

1. An anthracene derivative represented by a general formula (1),

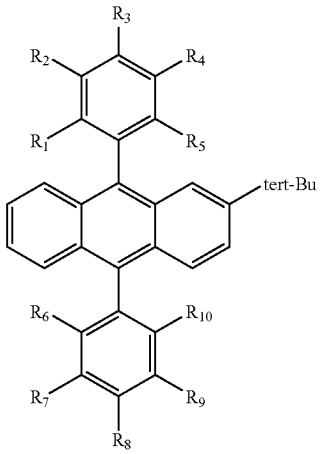

(1)

wherein $R^2$ and $R^7$ are a group represented by a structure formula (2), and $R^1$, $R^3$ to $R^5$, $R^6$, and $R^8$ to $R^{10}$ are individually any one of hydrogen and an alkyl group having 1 to 4 carbon atoms

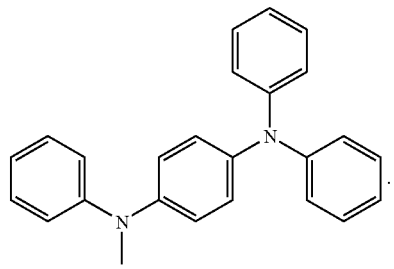

(2)

2. An anthracene derivative represented by a general formula (3),

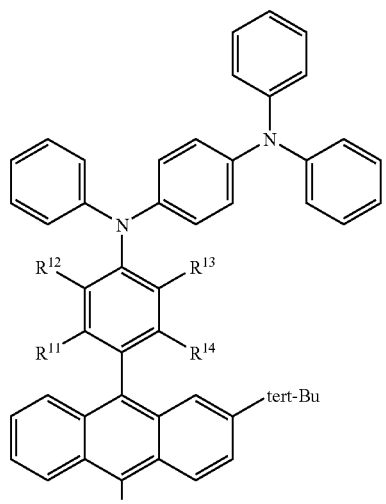

(3)

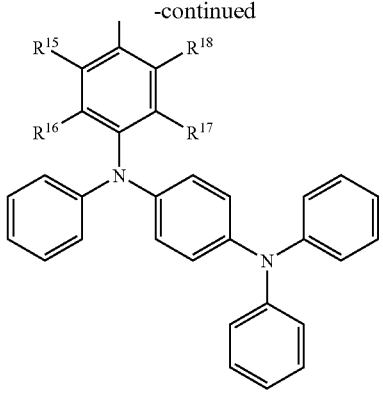

wherein $R^{11}$, $R^{13}$, $R^{16}$, and $R^{18}$ are an alkyl group having 1 to 4 carbon atoms, and $R^{12}$, $R^{14}$, $R^{15}$ and $R^{17}$ are individually any one of hydrogen and an alkyl group having 1 to 4 carbon atoms.

3. An anthracene derivative represented by a general formula (4),

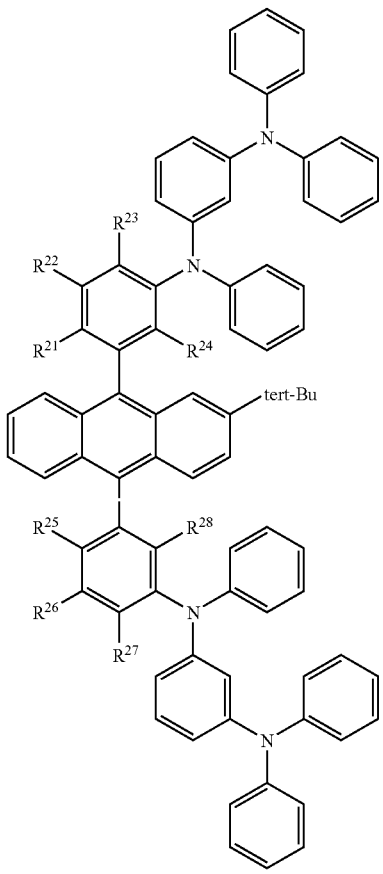

(4)

wherein $R^{21}$ to $R^{28}$ are individually any one of hydrogen and an alkyl group having 1 to 4 carbon atoms, and $R^{21}$ and $R^{22}$, $R^{22}$ and $R^{23}$, $R^{25}$ and $R^{26}$, and $R^{26}$ and $R^{27}$ may be individually bonded to form an aromatic ring.

4. An anthracene derivative represented by a general formula (5),

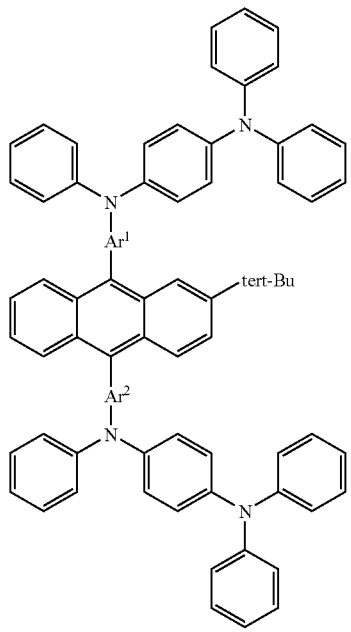

(5)

wherein Ar$^1$ and Ar$^2$ are individually an aryl group having 10 to 14 carbon atoms.

5. A light emitting device comprising:

a substrate;

a light emitting element formed over the substrate, the light emitting element comprising a pair of electrodes and a light emitting layer between the pair of electrodes, wherein the light emitting layer includes an anthracene derivative represented by a general formula (1), (1)

wherein R$^2$ and R$^7$ are a group represented by a structure formula (2), and R$^1$, R$^3$ to R$^5$, R$^6$, and R$^8$ to R$^{10}$ are individually any one of hydrogen and an alkyl group having 1 to 4 carbon atoms (2)

6. A light emitting device according to claim 5, wherein the light emitting device is incorporated into an electronic device selected from the group consisting of a personal computer, a cellular phone, and a television.

7. A light emitting device comprising:

a substrate;

a light emitting element formed over the substrate, the light emitting element comprising a pair of electrodes and a light emitting layer between the pair of electrodes, wherein the light emitting layer includes an anthracene derivative represented by a general formula (3), (3)

wherein R$^{11}$, R$^{13}$, R$^{16}$, and R$^{18}$ are an alkyl group having 1 to 4 carbon atoms, and R$^{12}$, R$^{14}$, R$^{15}$, and R$^{17}$ are individually any one of hydrogen and an alkyl group having 1 to 4 carbon atoms.

8. A light emitting device according to claim 7,
wherein the light emitting device is incorporated into an electronic device selected from the group consisting of a personal computer, a cellular phone, and a television.

9. A light emitting device comprising:
a substrate;
a light emitting element formed over the substrate, the light emitting element comprising a pair of electrodes and a light emitting layer between the pair of electrodes,
wherein the light emitting layer includes an anthracene derivative represented by a general formula (4),

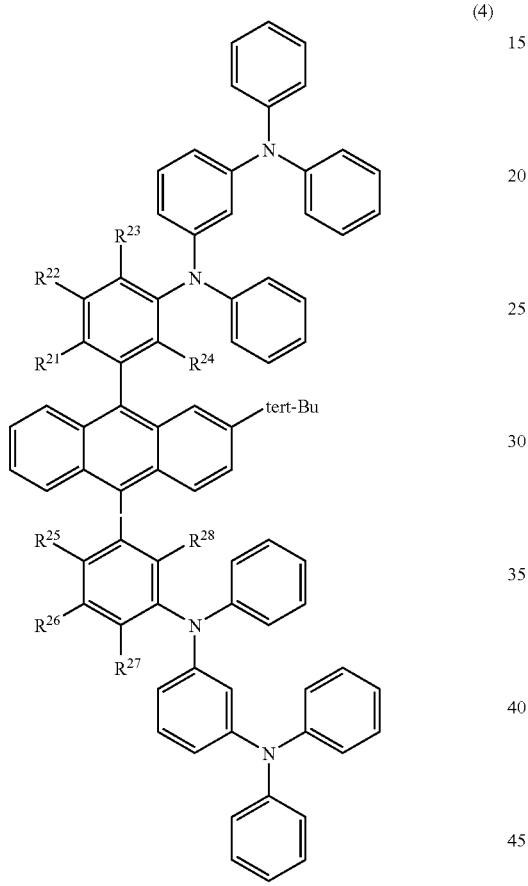

(4)

wherein $R^{21}$ to $R^{28}$ are individually any one of hydrogen and an alkyl group having 1 to 4 carbon atoms, and $R^{21}$ and $R^{22}$, $R^{22}$ and $R^{23}$, $R^{25}$ and $R^{26}$, and $R^{26}$ and $R^{27}$ may be individually bonded to form an aromatic ring.

10. A light emitting device according to claim 9,
wherein the light emitting device is incorporated into an electronic device selected from the group consisting of a personal computer, a cellular phone, and a television.

11. A light emitting device comprising:
a substrate;
a light emitting element formed over the substrate, the light emitting element comprising a pair of electrodes and a light emitting layer between the pair of electrodes,
wherein the light emitting layer includes an anthracene derivative represented by a general formula (5),

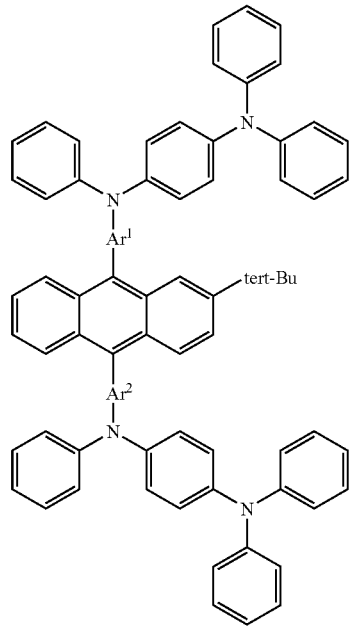

(5)

wherein $Ar^1$ and $Ar^2$ are individually an aryl group having 10 to 14 carbon atoms.

12. A light emitting device according to claim 11,
wherein the light emitting device is incorporated into an electronic device selected from the group consisting of a personal computer, a cellular phone, and a television.

13. An anthracene derivative according to claim 4,
wherein $Ar^1$ and $Ar^2$ are the same to each other and selected from

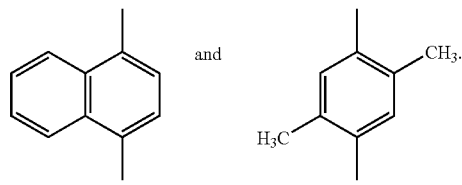

14. A light emitting device according to claim 11,
wherein $Ar^1$ and $Ar^2$ are the same to each other and selected from

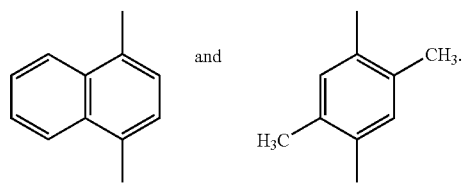

* * * * *